United States Patent
Wong et al.

(10) Patent No.: US 8,268,969 B2
(45) Date of Patent: Sep. 18, 2012

(54) GLOBO H AND RELATED ANTI-CANCER VACCINES WITH NOVEL GLYCOLIPID ADJUVANTS

(75) Inventors: Chi-Huey Wong, La Jolla, CA (US); Chung-Yi Wu, Taipei (TW); Alice L. Yu, La Jolla, CA (US); John Yu, La Jolla, CA (US)

(73) Assignee: Academia Sinica, Taipei (TW)

( * ) Notice: Subject to any disclaimer, the term of this patent is extended or adjusted under 35 U.S.C. 154(b) by 216 days.

(21) Appl. No.: 12/537,129

(22) Filed: Aug. 6, 2009

(65) Prior Publication Data

US 2010/0136042 A1 Jun. 3, 2010

(51) Int. Cl.
*C07K 16/00* (2006.01)
*A01N 43/04* (2006.01)
*C07H 17/00* (2006.01)

(52) U.S. Cl. ............... 530/387.1; 530/391.7; 530/391.9; 530/395; 514/25; 536/17.9

(58) Field of Classification Search ............... 424/178.1, 424/184.1, 193.1; 435/7.29; 514/25
See application file for complete search history.

(56) References Cited

U.S. PATENT DOCUMENTS

2008/0254045 A1* 10/2008 Donda et al. ............... 424/178.1
2009/0324619 A1* 12/2009 Hwang et al. ............... 424/178.1

OTHER PUBLICATIONS

Zhu J. et al. (2009) J. Am. Chem. Soc. 131(26):9298-9303).*
Wu et al. (J. Org. Chem. 2005, 70: 7381-7388).*
Kageyama et al. (J. Biochem. 2007, 142: 95-104).*

* cited by examiner

*Primary Examiner* — Peter J Reddig
*Assistant Examiner* — Yan Xiao
(74) *Attorney, Agent, or Firm* — Occhiuti Rohlicek & Tsao LLP

(57) ABSTRACT

Immunogenic compositions, cancer vaccines and methods for treating cancer are provided. Compositions comprising: (a) a glycan such as Globo H or an immunogenic fragment thereof, wherein the glycan is conjugated with a carrier protein by a linker such as para-nitrophenyl; and (b) an adjuvant comprising glycolipid capable of binding CD1d on a dendritic cell, such as an α-galactosyl-ceramide derivative, wherein the immunogenic composition induces an immune response that induces a higher relative level of IgG isotype antibodies as compared to IgM isotype antibodies, are provided. Immunogenic compositions comprising the carrier protein diphtheria toxin cross-reacting material 197 (DT-CRM197) and the adjuvant C34 are provided. Antibodies generated by immunogenic compositions disclosed herein further neutralize at least one of the antigens Globo H, stage-specific embryonic antigen-3 (SSEA-3) and stage-specific embryonic antigen-4 (SSEA-4). Therapeutics against breast cancer stem cells comprising immunogenic compositions comprising Globo H, SSEA-3 or SSEA-4 conjugated with DT-CRM197.

19 Claims, 18 Drawing Sheets
(11 of 18 Drawing Sheet(s) Filed in Color)

C1, R = (CH$_2$)$_{24}$CH$_3$
C23, R = (CH2)$_7$PhF
C34, R = (CH$_2$)$_{10}$PhOPhF
7DW8-5, R = (CH$_2$)$_{10}$PhF

Figure 12 (B)

Gb5-DT adjuvant/C1 anti-Gb5 IgG

GLOBO H AND RELATED ANTI-CANCER VACCINES WITH NOVEL GLYCOLIPID ADJUVANTS

CROSS-REFERENCE TO RELATED APPLICATIONS

This patent application is related to co-pending U.S. patent application Ser. No. 12/485,546, titled "Compositions for inducing immune responses specific to Globo H and SSEA-3 and uses thereof in cancer treatment" filed Jun. 16, 2009, which claims priority to U.S. Provisional Patent Application Ser. No. 61/061,968, filed Jun. 16, 2008. The contents of these patent applications are incorporated herein in their entirety by reference.

TECHNICAL FIELD OF THE INVENTION

This invention relates to the field of cancer vaccines. In particular, the application relates to a carbohydrate-based vaccine containing the B cell epitope, Globo H, which is conjugated to the immunogenic carrier DT-CRM197. More particularly, the invention is directed at anti-cancer Globo H-DT vaccines administered with novel glycolipid adjuvants, such as C34.

BACKGROUND OF THE INVENTION

To design therapy against cancer, it is desirable to seek molecular targets of cancer or cancer stem cells that are absent from normal cells. Aberrant glycosylation is often associated with tumor progression and was first described by Meezan et al. in 1969 with the demonstration that cancer glycans differ from healthy cells. (Meezan E, et al. (1969) *Biochemistry* 8:2518-2524.) Aberrant glycosylations include loss or over-expression of certain structures, the persistence of truncated structures and the emergence of novel structures. The structural differences were later supported by many histological evidences using lectin-staining compared with healthy and malignant tissue. (Turner G A (1992) *Clin Chim Acta* 208:149-171; Gabius H J (2000) *Naturwissenschaften* 87:108-121.)

More recently, tumor associated carbohydrate antigens were identified by monoclonal antibodies and mass spectrometry. (Shriver Z, et al. (2004) *Nat Rev Drug Disc* 3:863-873; Pacino G, et al. (1991) *Br J Cancer* 63:390-398.) To date, numerous tumor associated antigens expressed on cancer cells in the form of glycolipids or glycoproteins have been characterized and correlated to certain types of cancers. (Bertozzi C R, Dube D H (2005) *Nat Rev Drug Discovery* 4:477-488.) Although relatively little is known about the role of surface carbohydrates play in malignant cells, passively administered or vaccine induced antibodies against these antigens have correlated with improved prognosis.

Of the tumor associated glycans reported, the glycolipid antigen Globo H (Fucα1→2 Galβ1→3 GalNAcβ1→3 Galα1→4 Galβ1→4 Glc) was first isolated and identified in 1984 by Hakomori et al. from breast cancer MCF-7 cells. (Bremer E G, et al. (1984) *J Biol Chem* 259:14773-14777.) Further studies with anti-Globo H monoclonal antibodies showed that Globo H was present on many other cancers, including prostate, gastric, pancreatic, lung, ovarian and colon cancers and only minimal expression on luminal surface of normal secretory tissue which is not readily accessible to immune system. (Ragupathi G, et al. (1997) *Angew Chem Int Ed* 36:125-128.) In addition, it has been established that the serum of breast cancer patient contains high level of anti-Globo H antibody. (Gilewski T et al. (2001) *Proc Natl Acad Sci USA* 98:3270-3275; Huang C-Y, et al. (2006) *Proc Natl Acad Sci USA* 103:15-20; Wang C-C, et al. (2008) *Proc Natl Acad Sci USA* 105(33):11661-11666) and patients with Globo H-positive tumors showed a shorter survival in comparison to patients with Globo H-negative tumors. (Chang, Y-J, et al. (2007) *Proc Natl Acad Sci USA* 104(25):10299-10304.) These findings render Globo H, a hexasaccharide epitope, an attractive tumor marker and a feasible target for cancer vaccine development.

Globo H is a cancer antigen overly expressed in various epithelial cancers. It has been suggested that this antigen can serve as a target in cancer immunotherapy. While vaccines have been developed to elicit antibody responses against Globo H, their anti-cancer efficacies are unsatisfactory due to low antigenicity of Globo H. There is a need for a new vaccine capable of eliciting high levels of immune responses targeting Globo H.

Stem cells are defined as a group of cells with the capacity for self-renewal and for differentiation into different types of cells and tissues. (Reya T et al., (2001) *Nature* 414:105-111.) As both malignant tumors and normal tissues contain heterogeneous populations of cells, cancer stem cells might play a key role in tumor growth and maintaining tumor heterogeneity. Cancer stem cells have been identified from a variety of solid tumors, such as brain, breast, colon, and prostate cancers. Breast cancer stem cells (BCSCs) were first shown to reside in the CD24$^-$CD44$^+$ subpopulation of breast cancer by Al-Hajj et al., based on their ability to generate tumors with phenotypic diversity on xenotransplantation into NOD/SCID mice (Al-Hajj M, et al., (2003) *Proc Natl Acad Sci USA* 100:3983-3988). The majority of early disseminated cancer cells in the bone marrow of breast cancer patients displayed the phenotype of CD24$^-$CD44$^+$ (Balic M et al., (2006) *Clin Cancer Res* 12:5615-5621), suggesting that BCSCs were capable of metastasis. Based on their capability for growth, differentiation, and metastasis and their resistance to radiation, BCSCs are a major target for therapy of breast cancer (Tang C. et al., (2007) *FASEB J.* 21:1-9).

In breast cancer, Globo H expression was observed in >60% of ductal, lobular, and tubular carcinoma, but not in nonepithelial breast tumors (Mariani-Constantini R et al., (1984) *Am. J. Pathol.* 115:47-56). Globo H is not expressed in normal tissue except for weak expression in the apical epithelial cells at lumen borders, a site that appears to be inaccessible to the immune system (Id.; Zhang S. et al., (1997) *Int. J. Cancer* 73:42-49).

Globo H also is expressed in breast cancer stem cells (BCSCs). Flow cytometry revealed Globo H is expressed in 25/41 breast cancer specimens (61.0%). Non-BCSCs from 25/25 and BCSCs from 8/40 (20%) express Globo H. The stage-specific embryonic antigen 3 (SSEA-3), the pentasaccharide precursor of Globo H, is expressed in 31/40 (77.5%) tumors. Non-BCSCs from 29/31 and BCSCs from 25/40 (62.5%) expressed SSEA-3. (Chang W-W. et al., (2008) *Proc Natl Acad Sci USA* 105(33):11667-11672.)

Danishefsky and Livingston previously reported the preparation of Globo H-KLH vaccine (Gilewski T et al. (2001) *Proc Natl Acad Sci USA* 98:3270-3275; Ragupathi G, et al. (1997) *Angew Chem Int Ed* 36:125-128; Kudryashov V, et al. (1998) *Glycoconj J.* 15:243-249; Slovin S F et al (1997) *Proc Natl Acad Sci USA* 96:5710-5715) and the heptavalent vaccine (containing GM2, Globo H, Lewis Y, Tn, STn, TF, and Tn-MUC1 individually conjugated to KLH; Sabbatini P J et al (2007) *Clin Cancer Res* 13:4170-4177) against a variety of cancers. However, patients immunized with the heptavalent vaccine induced antibody responses against only five of the seven antigens except GM2 and Lewis Y antibodies. Rather than ubiquitously expressed antigen such as GM2, Globo H exceptionally expressed on tumor cells with only minimal level on normal secretory tissue makes it a desirable target for vaccine development. In their studies, ozonolysis of Globo H aglycone was followed by reductive amination with KLH carrier protein to generate about 150 carbohydrate units per protein. (Ragupathi G, et al. (1997) *Angew Chem Int Ed* 36:125-128.) Further refinement increased the carbohydrate conjugation ratio to about 720:1 by using MMCCH linker. (Wang S-K, et al. (2008). *Proc Natl Acad Sci USA* 105:3690-3695.) However, it was difficult to precisely characterize the conjugated with a carrier protein through a linker; and (b) an adjuvant comprising a glycolipid capable of binding a CD1d molecule on a dendritic cell, wherein the immunogenic composition induces an immune response that induces a higher relative level of IgG isotype antibodies as compared to IgM isotype antibodies.

In some aspects, the carrier protein is diphtheria toxin cross-reacting material 197 (DT-CRM197). In some aspects, the linker is a p-nitrophenyl linker.

In some aspects, the adjuvant is a synthetic analog of α-galactosyl-ceramide (α-GalCer). In some embodiments the adjuvant is C34, wherein C34 comprises the structure:

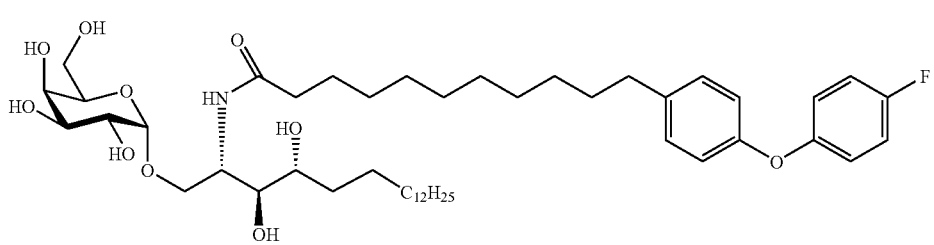

C34 glycoconjugate. In addition, the synthetic vaccine in combination with the immunological adjuvant QS-21 was shown to induce mainly IgM and to a lesser extent IgG antibodies in both prostate and metastatic breast cancer patients. In the phase I clinical trial, the vaccine also showed minimal toxicity with transient local skin reactions at the vaccination site. (Gilewski T et al. (2001) *Proc Natl Acad Sci USA* 98:3270-3275; Ragupathi G, et al. (1997) *Angew Chem Int Ed* 36:125-128; Slovin S F et al (1997) *Proc Natl Acad Sci USA* 96:5710-5715.) Mild flu-like symptoms which have been observed in some of the patients were probably associated with the side effect of QS-21. A pentavalent vaccine containing five prostate and breast cancer associated carbohydrate antigens—Globo-H, GM2, STn, TF and Tn—conjugated to maleimide-modified carrier protein KLH has been reported to produce anti-Globo H sera with higher titers of IgG than IgM in ELISA assays. (Zhu J. et al. (2009) *J. Am. Chem. Soc.* 131 (26):9298-9303).

Therefore, it is desirable to identify an alternative carrier and adjuvant to augment the antibody response to Globo H, especially with high titer of IgG, and to improve the vaccine efficacy with minimal side effects.

SUMMARY OF THE INVENTION

This invention relates to a carbohydrate based vaccine containing Globo H (B cell epitope) chemically conjugated to the immunogenic carrier diphtheria toxin cross-reacting material 197 (DT-CRM197) (Th epitope) via a p-nitrophenyl linker. The synthetic vaccine in combination with a glycolipid adjuvant induce IgG, IgG1 and IgM antibodies and provided an exceptional immunogenicity in breast cancer models, showing delayed tumorigenesis in xenograft studies. Glycan array analysis of the antibodies induced by Globo H-DT and the glycolipid C34 showed that the antibodies not only recognized Globo H but also SSEA-3 (Gb5) and SSEA-4 (sialyl Gb5) glycans, all specific for cancer cells and cancer stem cells.

The invention relates to an immunogenic composition comprising: (a) a glycan consisting essentially of Globo H or an immunogenic fragment thereof, wherein the glycan is In some aspects, the immune response is preferably oriented towards the production of IgG isotype antibodies. In some aspects, the immunogenic composition comprises at least one adjuvant able to induce a humoral and cellular immune response.

In some aspects, the antibodies generated by the immune response neutralize antigens expressed on cancer cells or cancer stem cells. In some embodiments, the antibodies generated by the immune response neutralize at least one of the antigens Gb4, stage-specific embryonic antigen-3 (SSEA-3) and stage-specific embryonic antigen-4 (SSEA-4). In some embodiments, the antibodies that neutralize at least one of the antigens Gb4, stage-specific embryonic antigen-3 (SSEA-3) and stage-specific embryonic antigen-4 (SSEA-4) comprise a higher relative level of IgG isotype antibodies as compared to IgM isotype antibodies.

The invention relates to a cancer vaccine comprising the immunogenic composition which is able to induce anti-cancer immune responses in a subject. In some aspects, the cancer vaccine is suitable for treating a cancer selected from the group consisting of: breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

In some aspects, the cancer tissue expresses a Globo H antigen on the surface of the cell. In some aspects, the Globo H antigen is expressed on an epithelial cell of a breast tumor.

In some embodiments, the cancer vaccine generates antibodies that neutralize at least one of the antigens Globo H, Gb4, stage-specific embryonic antigen-3 (SSEA-3) and stage-specific embryonic antigen-4 (SSEA-4). In some aspects, the antigens are expressed on a breast cancer stem cell.

The invention relates to a method of treatment comprising inhibition of tumor growth, the method comprising: (a) administering to a subject in need thereof, an immunogenic composition comprising: a glycan consisting essentially of Globo H or an immunogenic fragment thereof, wherein the glycan is conjugated with a carrier protein through a linker, and an adjuvant comprising a glycolipid capable of binding a CD1d molecule on a dendritic cell; and (b) inducing an immune response that induces a higher relative amount of IgG isotype antibodies as compared to IgM isotype antibodies.

In some embodiments of the method, the linker is p-nitrophenol, the carrier protein is diphtheria toxin cross-reacting material 197 (DT-CRM197) and the adjuvant is a synthetic analog of α-galactosyl-ceramide (α-GalCer). In one embodiment, the adjuvant is C34.

In some embodiments of the method, the immunogenic composition further comprises a cancer vaccine, and further wherein one or more treatments with an effective amount of the cancer vaccine inhibits tumor growth. In some embodiments, administration of the cancer vaccine reduces the size of a tumor.

In some embodiments of the method, wherein the immune response is preferably oriented towards the production of IgG isotype antibodies that neutralize at least one of the antigens Globo H, Gb4, stage-specific embryonic antigen-3 (SSEA-3) and stage-specific embryonic antigen-4 (SSEA-4). In some aspects, at least one of the antigens Globo H, stage-specific embryonic antigen-3 (SSEA-3) and stage-specific embryonic antigen-4 (SSEA-4) is expressed on a breast cancer stem cell. In some aspects, the Globo H antigen is expressed on an epithelial cell of a breast tumor.

The invention relates to a cancer vaccine comprising: (a) an immunogenic composition comprising: a glycan consisting essentially of Globo H or an immunogenic fragment thereof, wherein the glycan is conjugated with a carrier protein through a linker, and an adjuvant comprising a glycolipid capable of binding a CD1d molecule on a dendritic cell, wherein the immunogenic composition induces an immune response that induces a higher relative level of IgG isotype antibodies as compared to IgM isotype antibodies; and (b) a pharmaceutically acceptable excipient.

In some aspects, the cancer vaccine comprises an immunogenic composition the linker is p-nitrophenol, the carrier protein is diphtheria toxin cross-reacting material 197 (DT-CRM197) and the adjuvant is a synthetic analog of α-galactosyl-ceramide (α-GalCer). In one embodiment, the adjuvant is C34.

In some aspects, the cancer vaccine is used to treat a cancer, wherein one or more treatments with an effective amount of the cancer vaccine inhibits tumor growth. In some embodiments, administration of the cancer vaccine reduces the size of a tumor. In some embodiments, the cancer is selected from the group consisting of: breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, intestinal cancer, and bladder cancer.

The invention relates to an immunogenic composition comprising: (a) a glycan consisting essentially of a Globo H-related glycan or an immunogenic fragment thereof, wherein the glycan is conjugated with a carrier protein through a linker; and (b) an adjuvant comprising a glycolipid capable of binding a CD1d molecule on a dendritic cell, wherein the Globo H-related glycan is selected from the group consisting of SSEA-3 and SSEA-4, and wherein the immunogenic composition induces an immune response that induces a higher relative level of IgG isotype antibodies as compared to IgM isotype antibodies.

In some aspects of the immunogenic composition the carrier protein is diphtheria toxin cross-reacting material 197 (DT-CRM197), the adjuvant is a synthetic analog of α-galactosyl-ceramide (α-GalCer) and the linker is a p-nitrophenyl linker. In one embodiment, the adjuvant is C34

The invention relates to a therapeutic against breast cancer stem cells, the therapeutic comprising: Globo H conjugated through a p-nitrophenyl linker with a diphtheria toxin cross-reacting material 197 (DT-CRM197) carrier protein; and an adjuvant comprising a glycolipid capable of binding a CD1d molecule on a dendritic cell. In some embodiments of the therapeutic, the adjuvant is C34.

The invention relates to a therapeutic against breast cancer stem cells, the therapeutic comprising: SSEA-3 conjugated through a p-nitrophenyl linker with a diphtheria toxin cross-reacting material 197 (DT-CRM197) carrier protein; and an adjuvant comprising a glycolipid C34 capable of binding a CD1d molecule on a dendritic cell.

The invention relates to a therapeutic against breast cancer stem cells, the therapeutic comprising: SSEA-4 conjugated through a p-nitrophenyl linker with a diphtheria toxin cross-reacting material 197 (DT-CRM197) carrier protein. In some embodiments, the therapeutic further comprises an adjuvant comprising a glycolipid capable of binding a CD1d molecule on a dendritic cell.

Administration of the therapeutics of the invention to a subject induces production of antibodies that recognize an antigen expressed on a breast cancer stem cell (BCSC), wherein the antigen is selected from the group consisting of Globo H, SSEA-3 and SSEA-4. The invention relates to a method of treating breast cancer comprising administration of a therapeutic of the invention.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 12A: anti-Globo H IgG induced by Globo H-DT with C1 adjuvant; FIG. 12B: anti-Gb5 IgG induced by Gb5-DT with C1 adjuvant; FIG. 12C: anti-SSEA-4 IgG induced by SSEA-4-DT with C1 adjuvant.

DETAILED DESCRIPTION OF THE INVENTION

Figure 1:
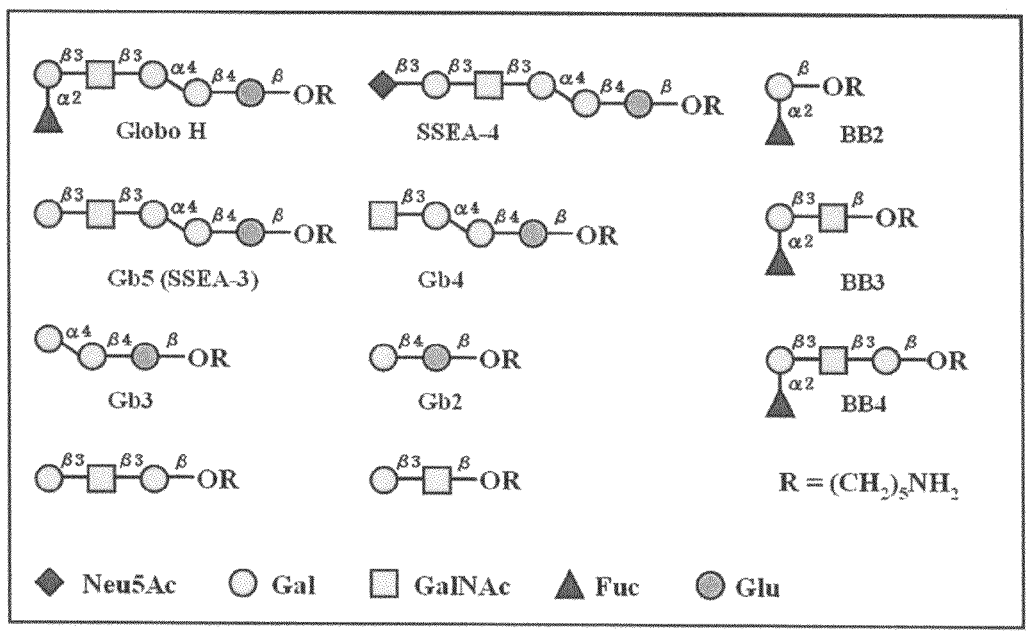
FIG. 1 shows structures of Globo H and truncated derivatives.

The present invention relates to the surprising finding that DT-CRM197 is a promising carrier protein for Globo H and SSEA-4 not only because it has been widely used for human vaccination against diphtheria for decades, but also because of its highly immunogenic property. Most importantly, it has been approved by the FDA for various glycoconjugate vaccines. Diphtheria toxin cross-reacting material 197 (DT-CRM 197) is a nontoxic mutant (G52E) of DT that shares the immunological properties of the native molecule and its ability to bind to heparin-binding, epidermal growth factor (HB-EGF), the specific cell-membrane receptor for DT that is often overexpressed in cancer. (Buzzi S. et al., Cancer Immunology, Immunotherapy (2004), 53(11):1041-1048).

Using C34 as adjuvant, both GH-DT and SSEA-4-DT showed the most effective immune response to induce more IgG than IgM antibodies against tumor antigens. The GH-DT in combination with C34 induced antibodies which not only neutralize Globo H but also SSEA-3 (Gb5) and SSEA-4, which all are specific for breast cancer cells and the cancer stem cells.

Further, the disclosed glycan microarray offers a powerful platform for antibody specificity test and is useful for identification of patients for the vaccine trial and for the monitoring of their immune response after immunization.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

DEFINITIONS

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

As used herein, the term "lipid" refers to any fat-soluble (lipophilic) molecule that participates in cell signaling pathways.

As used herein, the term "glycolipid" refers to a carbohydrate-attached lipid that serves as a marker for cellular recognition.

As used herein, the term "alpha-galactosyl ceramide" and "α-GalCer" refers to a glycolipid that stimulates natural killer T cells to produce both T helper (TH)1 and TH2 cytokines. As used herein, the glycolipid derivative C34 has the following structure:

As used herein, the term "glycoprotein" refers to a protein covalently modified with glycan(s). There are four types of glycoproteins: 1) N-linked glycoproteins, 2) O-linked glycoproteins (mucins), 3) glucosaminoglycans (GAGs, which are also called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "antigen" is defined as any substance capable of eliciting an immune response.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

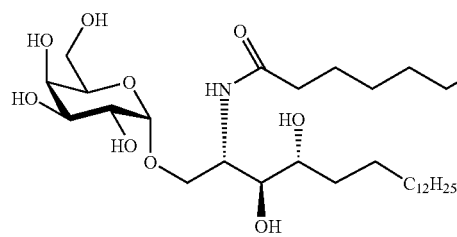

C34

The α-GalCer analogs of the present disclosure include α-GalCer analogs of bacterial origin (Group I: C2, C3 and C14), α-GalCer analogs modified with sulfonation (Group II: C4, C5 and C9), phenyl-alkyl chain α-GalCer analogs (Group III: C6-C8, C10-C11, C15-C16, C18-C34, C8-5 and C8-6) and phytosphingosine truncated α-GalCer analogs (Group IV: C12, C13 and C17). The structures of C34 and other alpha-galactosyl ceramide analogs and their use as adjuvants are disclosed in detail in PCT patent Application No. PCT/US2008/060275 filed Apr. 14, 2008.

The synthetic α-GalCer analogs, including C34, are capable of forming complexes with a CD1d molecule. Synthetic α-GalCer analogs are capable of being recognized by NKTs T-cell receptors. Synthetic α-GalCer analogs are capable of eliciting a $T_H1$-type, a $T_H2$-type or a TH1-type and a TH2-type response. The α-GalCer analogs are capable of activating NKTs in vitro. α-GalCer analogs are capable of activating NKTs in vivo.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "immunotherapy" refers to an array of treatment strategies based upon the concept of modulating the immune system to achieve a prophylactic and/or therapeutic goal.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids, including α-GalCer analogs such as C34.

As used herein, the term "adaptive immune system" refers to highly specialized, systemic cells and processes that eliminate pathogenic challenges. The cells of the adaptive immune system are a type of leukocyte, called a lymphocyte. B cells and T cells are the major types of lymphocytes.

As used herein, the term "T cells" and "Ts" refer to a group of white blood cells known as lymphocytes, that play a central role in cell-mediated immunity. T cells can be distinguished from other lymphocyte types, such as B cells and NKs by the presence of a special receptor on their cell surface called the T cell receptor (TCR). Several different subsets of T cells have been described, each with a distinct function. Helper T ($T_H$) Cells are the "middlemen" of the adaptive immune system. Once activated, they divide rapidly and secrete small proteins called cytokines that regulate or "help" the immune response. Depending on the cytokine signals received, these cells differentiate into $T_H1$, $T_H2$, $T_H17$, or one of other subsets, which secrete different cytokines.

As used herein, the term "antigen-presenting cell" (APC) refers to a cell that displays foreign antigen complexed with major histocompatibility complex (MHC) on its surface. T-cells may recognize this complex using their TCR. APCs fall into two categories: professional or non-professional. Dendritic cells (DCs) fall under the professional category and are capable of presenting antigen to T cells, in the context of CD1. In an exemplary implementation, the DCs utilized in the methods of this disclosure may be of any of several DC subsets, which differentiate from, in one implementation, lymphoid or, in another implementation, myeloid bone marrow progenitors.

As used herein, the term "naïve cell" refers to an undifferentiated immune system cell, for example a CD4 T-cell, that has not yet specialized to recognize a specific pathogen.

As used herein, the term "natural killer cells" and "NKs" refers to a class of lymphoid cells which are activated by interferons to contribute to innate host defense against viruses and other intracellular pathogens.

As used herein, the term "natural killer T cells" (NKTs) refers to a subset of T cells that share characteristics/receptors with both conventional Ts and NKs. Many of these cells recognize the non-polymorphic CD1d molecule, an antigen presenting molecule that binds self- and foreign lipids and glycolipids. The TCR of the NKTs are able to recognize glycolipid antigens presented (chaperoned) by a CD1d molecule. A major response of NKTs is rapid secretion of cytokines, including IL-4, IFN-$\gamma$ and IL-10 after stimulation and thus influence diverse immune responses and pathogenic processes. The NKTs may be a homogenous population or a heterogeneous population. In one exemplary implementation, the population may be "non-invariant NKTs", which may comprise human and mouse bone marrow and human liver T cell populations that are, for example, CD1d-reactive non-invariant T cells which express diverse TCRs, and which can also produce a large amount of IL-4 and IFN-$\gamma$. The best known subset of CD1d-dependent NKTs expresses an invariant TCR-alpha (TCR-$\alpha$) chain. These are referred to as type I or invariant NKTs (iNKTs). These cells are conserved between humans (V$\alpha$24i NKTs) and mice (V$\alpha$14i NKTs) and are implicated in many immunological processes.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-12, IL-18, IL-2, IFN-$\gamma$, TNF, IL-4, IL-10, IL-13, IL-21 and TGF-$\beta$.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C-C chemokines (RANTES, MCP-1, MIP-1$\alpha$, and MIP-1$\beta$), C-X-C chemokines (IL-8), C chemokines (Lymphotactin), and CXXXC chemokines (Fractalkine).

As used herein, the term "$T_H2$-type response" refers to a pattern of cytokine expression such that certain types of cytokines, interferons, chemokines are produced. Typical $T_H2$ cytokines include, but are not limited to, IL-4, IL-5, IL-6 and IL-10.

As used herein, the term "$T_H1$-type response" refers to a pattern of cytokine expression such that certain types of cytokines, interferons, chemokines are produced. Typical $T_H1$ cytokines include, but are not limited to, IL-2, IFN-$\gamma$, GMCSF and TNF-$\beta$.

As used herein, the term "$T_H1$ biased" refers to am immunogenic response in which production of $T_H1$ cytokines and/or chemokines is increased to a greater extent than production of $T_H2$ cytokines and/or chemokines.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "immunologic adjuvant" refers to a substance used in conjunction with an immunogen which enhances or modifies the immune response to the immunogen. The $\alpha$-GalCer analogs of the present disclosure are used as immunologic adjuvants to modify or augment the effects of a vaccine by stimulating the immune system of a patient who is administered the vaccine to respond to the vaccine more vigorously. In an exemplary implementation, the analog C34 is used as an adjuvant.

As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "anti-tumor immunotherapy active agent" refers to antibody generated by a vaccine of the of the present disclosure that inhibits, reduces and/or eliminates tumors.

As used herein, the term "antigen specific" refers to a property of a cell population such that supply of a particular antigen, or a fragment of the antigen, results in specific cell proliferation.

As used herein, the term "Flow cytometry" or "FACS" means a technique for examining the physical and chemical properties of particles or cells suspended in a stream of fluid, through optical and electronic detection devices.

Amino acid residues in peptides shall hereinafter be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W.H. Freeman & Co., New York 1983.

The compositions disclosed herein can be included in a pharmaceutical or nutraceutical composition together with additional active agents, carriers, vehicles, excipients, or auxiliary agents identifiable by a person skilled in the art upon reading of the present disclosure.

The pharmaceutical or nutraceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of the compositions disclosed herein according to the at least one of the above mentioned methods.

The kits possibly include also compositions comprising active agents, identifiers of a biological event, or other compounds identifiable by a person skilled upon reading of the present disclosure. The kit can also comprise at least one composition comprising an effective amount of the compositions disclosed herein or a cell line. The compositions and the cell line of the kits of parts to be used to perform the at least one method herein disclosed according to procedure identifiable by a person skilled in the art.

As used herein, the term "polypeptide" refers to any multimer or polymer of amino acid residues. A polypeptide may be composed of two or more polypeptide chains. A polypeptide includes a protein, a peptide, and an oligopeptide. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

Cancer Vaccines of the Invention

One embodiment of this invention is a method of treating cancer by administering to a subject in need thereof an effective amount of an immune composition containing either Globo H or a fragment thereof (e.g., stage specific embryonic antigen-3 (SSEA-3, also known as Gb5), or SSEA-4) and an adjuvant. The types of target cancer include, but are not limited to, breast cancer (including stages 1-4), lung cancer (e.g., small cell lung cancer), liver cancer (e.g., hepatocellular carcinoma), oral cancer, stomach cancer (including T1-T4), colon cancer, nasopharynx cancer, skin cancer, kidney cancer, brain tumor (e.g., astrocytoma, glioblastoma multiforme, and meningioma), prostate cancer, ovarian cancer, cervical cancer, bladder cancer, and endometrium, rhabdomyosarcoma, osteosarcoma, leiomyosarcoma, and gastrointestinal stromal tumor.

Cancers classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemias (lymphocytic leukemia; myeloid leukemia; monocytic leukemia; and other leukemias).

Other cancers, classified by histological type, that may be suitable targets for cancer vaccines according to the present invention include, but are not limited to, neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Bronchioloalveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

The term "treating" as used herein refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect the cancer, the symptoms of the cancer, or the predisposition toward the cancer. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The immune composition used in the above-described method can contain a glycan (i.e., a molecule containing a sugar moiety) that is Globo H or a fragment thereof and an adjuvant. Globo H is a glycan containing the hexasaccharide epitope (Fuc$\alpha$1→2 Gal$\beta$1→3 GalNAc$\beta$1→3 Gal$\alpha$1→4 Gal$\beta$1→4 Glc), and optionally, a non-sugar moiety. Its fragment is a glycan containing a fragment of the hexasaccharide epitope and, if applicable, the non-sugar moiety. These oligosaccharides can be prepared by routine methods. (See Huang et al., Proc. Natl. Acad. Sci. USA 103:15-20 (2006)). If desired, they can be linked to a non-sugar moiety.

The parent application U.S. patent application Ser. No. 12/485,546, was based on unexpected discoveries that (1) SSEA-3, the immediate precursor of Globo H, is expressed at a high level in breast cancer stem cells and therefore can serve as a suitable target for breast cancer treatment, and (2) $\alpha$-galactosyl-ceramide ($\alpha$-GalCer) is an effective adjuvant that promotes production of anti-Globo H and anti-SSEA-3 antibodies.

U.S. patent application Ser. No. 12/485,546 features an immune composition containing Globo H or its fragment (e.g., SSEA-3) and an adjuvant (e.g., $\alpha$-GalCer). Globo H or its fragment can be conjugated with Keyhole Limpet Hemocyanin (KLH). When administered into a subject (e.g., a human), this immune composition elicits immune responses (e.g., antibody production) targeting Globo H or its fragment and, therefore, is effective in treating cancer (e.g., breast cancer, prostate cancer, ovarian cancer, and lung cancer).

U.S. patent application Ser. No. 12/485,546 relates to a method of producing antibody specific to Globo H or its fragment by administering to a non-human mammal (e.g., mouse, rabbit, goat, sheep, or horse) the immune composition described above and isolating from the mammalian antibody that binds to Globo H or its fragment.

The Globo H or other glycans described in the instant disclosure is conjugated to a protein carrier, such as DT-CRM197. They can then be mixed with an adjuvant, such as C34 and optionally a pharmaceutically acceptable carrier (e.g., a phosphate buffered saline, or a bicarbonate solution) to form an immune composition (e.g., a vaccine) via conventional methods. See, e.g., U.S. Pat. Nos. 4,601,903; 4,599,231; 4,599,230; and 4,596,792. The composition may be prepared as injectables, as liquid solutions, or emulsions and the carrier is selected on the basis of the mode and route of administration, as well as on the basis of standard pharmaceutical practice. Suitable pharmaceutical carriers and diluents, and pharmaceutical necessities for their use, are described in Remington's Pharmaceutical Sciences. The immune composition preferably contains $\alpha$-GalCer as an adjuvant. Other examples of adjuvant include, but are not limited to, a cholera toxin, *Escherichia coli* heat-labile enterotoxin (LT), liposome, immune-stimulating complex (ISCOM), or immunostimulatory sequences oligodeoxynucleotides (ISS-ODN). The composition can also include a polymer that facilitates in vivo delivery. See Audran R. et al. Vaccine 21:1250-5, 2003; and Denis-Mize et al. Cell Immunol., 225:12-20, 2003. When necessary, it can further contain minor amounts of auxiliary substances such as wetting or emulsifying agents, or pH buffering agents to enhance the ability of the composition to elicit immune responses against the sugar moiety in Globo H or its fragment. The immune composition described herein can be administered parenterally (e.g., intravenous injection, subcutaneous injection or intramuscular injection). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immune composition described herein.

The immune composition described herein can be administered parenterally (e.g., intravenous injection, subcutaneous injection or intramuscular injection). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immune composition described herein.

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immune composition of this invention can also be used to generate antibodies in animals for production of antibodies, which can be used in both cancer treatment and diagnosis. Methods of making monoclonal and polyclonal antibodies and fragments thereof in animals (e.g., mouse, rabbit, goat, sheep, or horse) are well known in the art. See, for example, Harlow and Lane, (1988) *Antibodies: A Laboratory Manual*, Cold Spring Harbor Laboratory, New York. The term "antibody" includes intact immunoglobulin molecules as well as fragments thereof, such as Fab, F(ab')$_2$, Fv, scFv (single chain antibody), and dAb (domain antibody; Ward, et. al. (1989) *Nature*, 341, 544).

Globo H-DT-CRM197 and Related Vaccines

Figure 14:
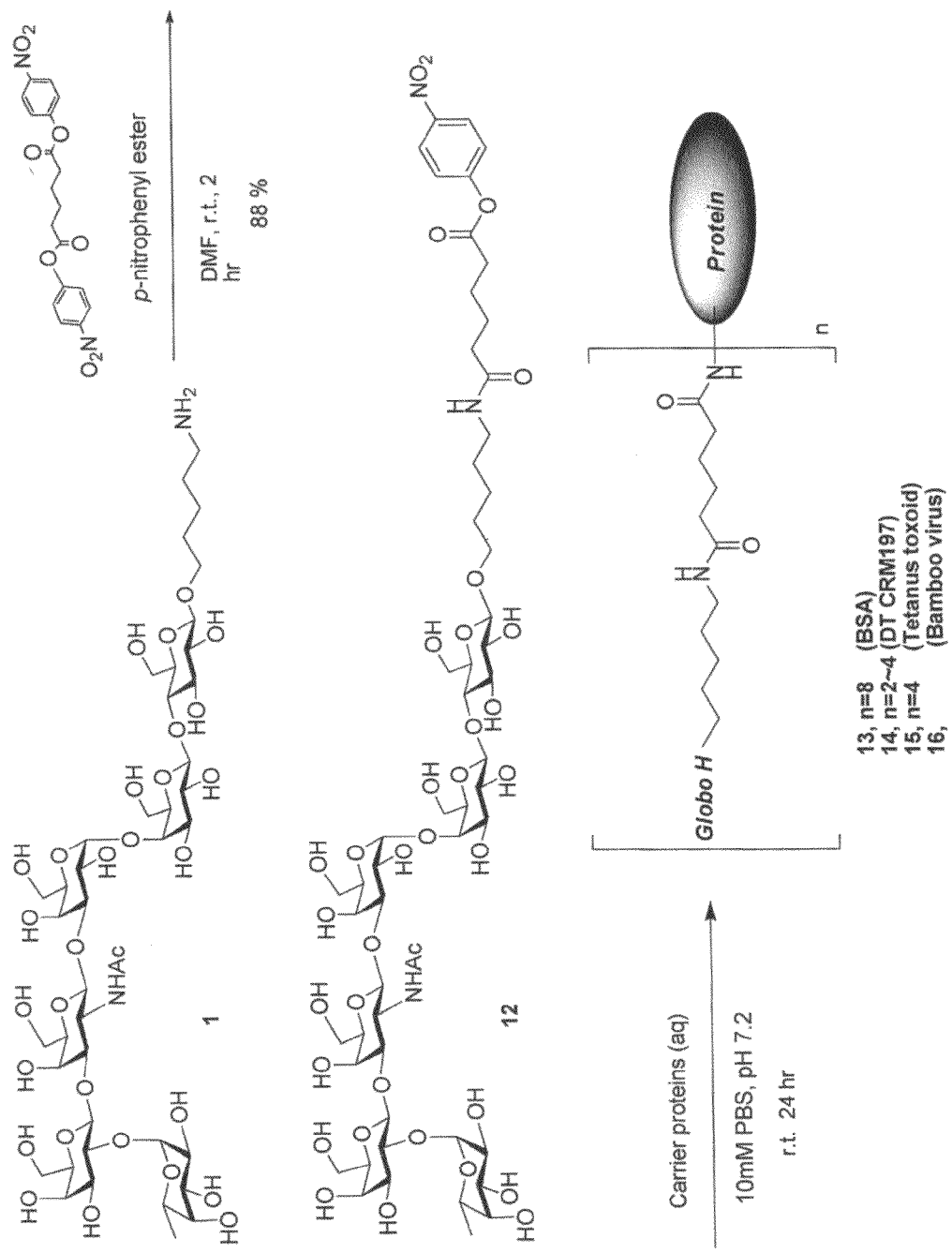
FIG. 14 shows a schematic for the synthesis of Globo H half ester and glycoconjugates.

Globo H (1) and its fragments 2-10 were synthesized by methods described herein. For protein conjugation, purified Globo H half ester 12 was incubated with individual carrier proteins as shown in FIG. 14.

The Globo H-protein conjugates were characterized by MALDI-TOF analysis to determine the number of Globo H molecules on each carrier protein. The average number of Globo H incorporation is listed in Table 1.

TABLE 1

MALDI-TOF analysis of Globo H incorporation.

| | Ref | Protein MW | After Glycosylation$^a$ | Average Incorporation (n) | Carbohydrate percentage |
|---|---|---|---|---|---|
| GH-BSA | 66431 | 66449 | 76029 | 8 | 14.4% |
| GH-DT | 58472 | 58326 | 62138 | 2~4 | 6.8% |
| GH-TT | 150682 | 155609 | 162902 | 6 | 4.5% |
| GH-KLH* | 8.6 × 10$^6$ | | | ~700 | 14.7% |
| GH-Bamboo | 25 kD × 1600 | | | N.D. | |

$^a$Peak m/z in MALDI-TOF;
N.D.: Not determined;
*GH-KLH was provided by Optimer Inc.

The GH-KLH conjugate showed the greatest number of Globo H incorporation, mostly due to the larger size and more Lys residues of KLH. The same coupling procedure using p-nitrophenyl linker was also applied to bamboo mosaic virus which contains more than 100,000 lysine residues on the coat of virus. However, the instability of the virus while reacting in sodium phosphate buffer (pH=7.2) at 4° C. is a major concern for further development. Additionally, the GH-BaMV 16 limits its detection by MALDI-TOF analysis due to its tremendous size.

The synthetic Globo H and truncated fragments (FIG. 1) were attached with a pentylamine linker at the reducing ends and covalently immobilized onto the NHS-coated glass slide. Nine of the eleven oligosaccharides were selected to be printed on the microarray. Each microarray slide was spotted with 50 µM of nine Globo H analogs (SSEA-4, GH, Gb5, Gb4, Gb3, Gb2, BB4, BB3, and BB2) respectively in 12 replications.

Figure 2A:
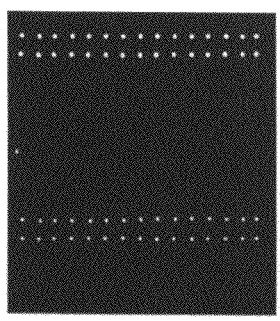
FIGS. 2A-2C show binding specificity of monoclonal antibodies VK9 and Mbr1 (to Globo H) and anti-SSEA-3, respectively.
Figure 2A:
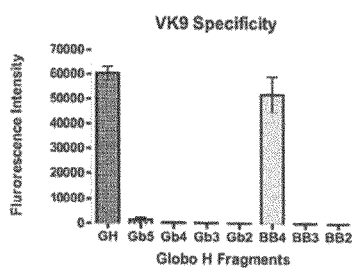
Figure 2B:
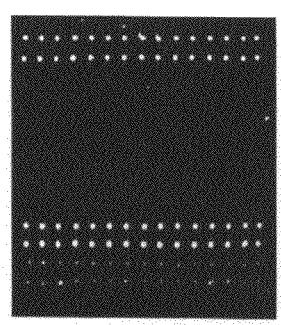
Figure 2B:
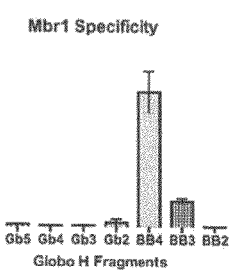
Figure 2C:
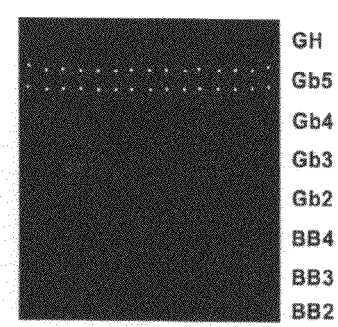
Figure 2C:
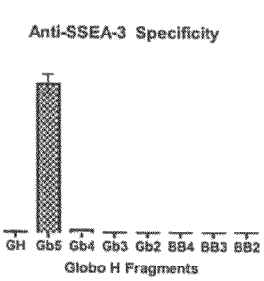

To validate the carbohydrates on the microarray, mouse monoclonal antibodies (VK9 and Mbr1 for Globo H, and anti-SSEA-3) were used and respective secondary antibodies (goat anti-mouse IgG and IgM) were used to examine the binding specificity, and the results are shown in FIG. 2A-2C. The data suggested that VK9 and Mbr1 both recognized Globo H and the outer tetrasaccharide BB4, though MBr1 also slightly recognized BB3. In addition, anti-SSEA-3 antibody specifically recognized SSEA-3 antigen (Gb5) without any cross reactivity. The results indicated that the Globo H microarray could be employed to profile the specificity and potency of polyclonal antibodies from immunized mice.

As previously reported, immunization of mice with a fully synthetic Globo H vaccine and co-administered with QS-21 resulted in the generation of antibodies against human breast cancer cells; however the mouse antibodies are mainly IgM, even after several boosting vaccinations. (Ragupathi G, et al. (1997) *Angew Chem Int Ed* 36:125-128).

Figure 3A:
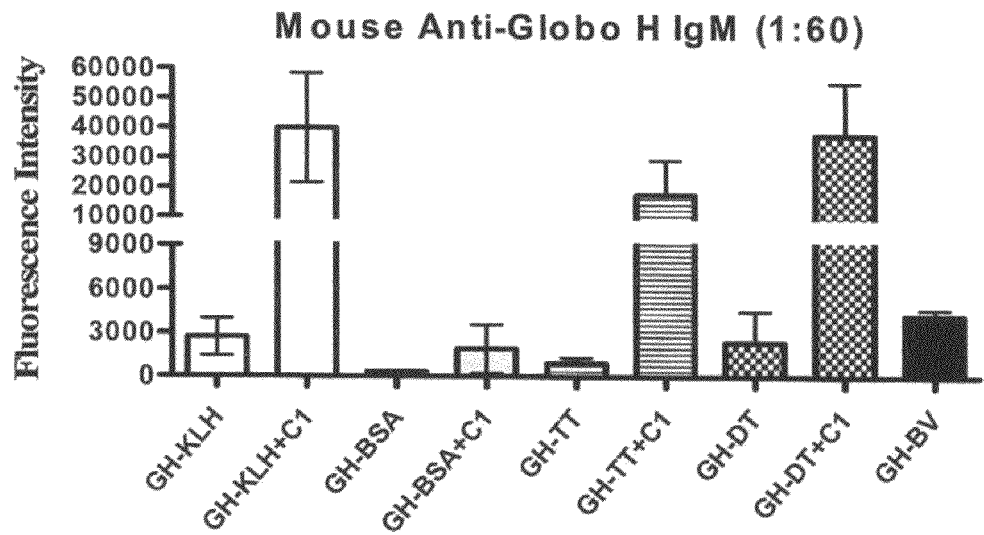
FIGS. 3A-3B show serologic response of mice vaccinated with various Globo H conjugates and α-GalCer. Groups of three C57BL/6 mice were vaccinated s.c. with 1 µg of synthetic glycoconjugates with or without 2 µg glycolipid. Mice sera were diluted 1:60 and 1:240 respectively for IgM (FIG. 3A) and IgG (FIG. 3B) antibody analysis. Cy3-anti-mouse IgG or IgM secondary antibodies were used for fluorescence detection under 532 nm, PMT 500, Data represent as average fluorescence intensity of three mice±the SEM.
Figure 3B:
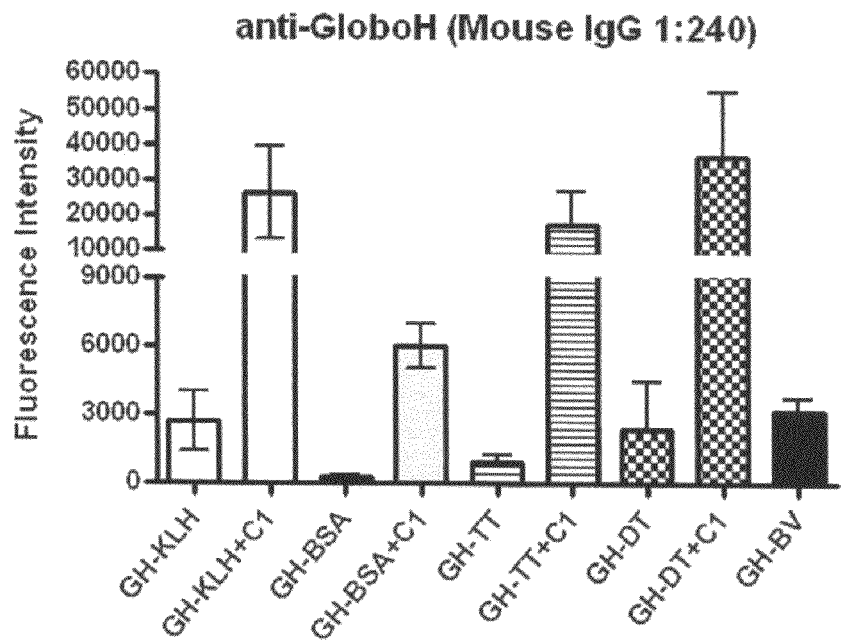

A group of mice were immunized with 1 µg synthetic Globo H-conjugates with or without the glycolipid adjuvant, α-GalCer (C1) subcutaneously. It was found that GH-KLH, GH-DT and GH-BV are the most effective immunogens for IgM induction, followed by GH-TT, and GH-BSA as summarized in FIG. 3A, and α-GalCer is capable of stimulating the immune response to induce high levels of IgM antibodies. A similar trend was also observed in mouse IgG antibodies (FIG. 3B), and the relative IgG levels were higher than IgM levels. In brief, despite the lower carbohydrate density of the synthetic glycoconjugate, GH-DT exhibited a similar immunogenicity to GH-KLH, and the adjuvant α-GalCer was shown to enhance the immune response.

Figure 4:
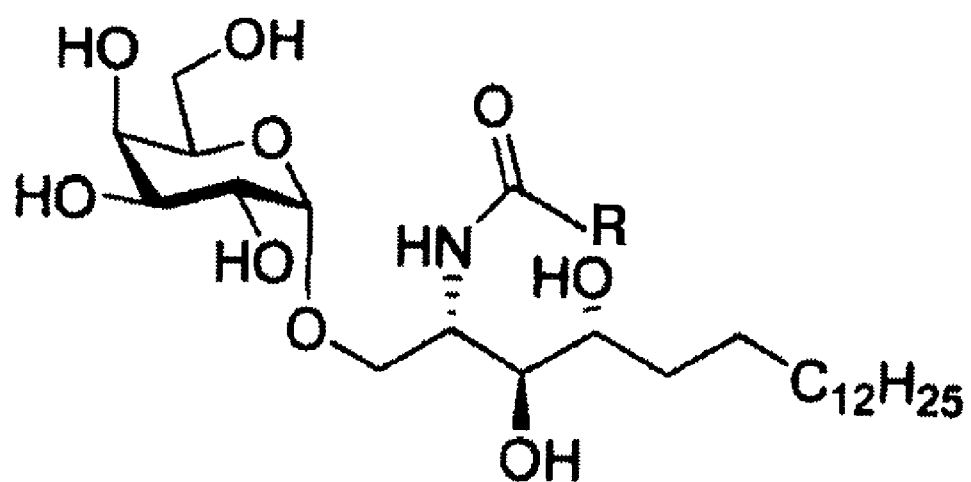
FIG. 4 shows structures of α-GalCer and analogues
Figure 5:
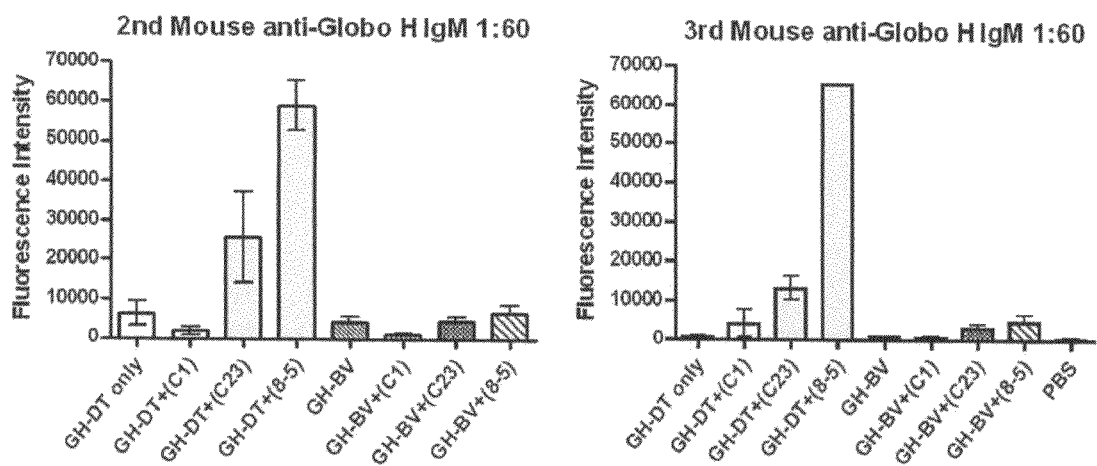
FIG. 5 shows IgM levels of mice vaccinated with Globo H conjugates and α-GalCer derivatives. Mouse sera were collected and analyzed after $2^{nd}$ and $3^{rd}$ vaccinations, as shown. Cy3 secondary anti-mouse IgM was used for detection under 532 nm, PMT 400. The results represent average fluorescence intensity of three mice±the SEM.

Since β-GalCer has been shown to be an effective adjuvant for GH-DT, other glycolipids with better adjuvant activity than C1 were examined as shown in FIG. 4. Groups of mice were immunized with GH-DT and GH-BV with or without glycolipids. Sera were obtained and introduced to glycan microarray analysis. In general, mouse anti-Globo H IgG titers increased as immunization proceeded but the IgM levels were almost independent of vaccination times (FIG. 5). Among the GH-BV vaccinated groups, there is no significant difference in the IgM level between glycolipid-vaccine treatment and the vaccine alone. Although the results suggested that GH-BV in combination with glycolipid was not an effective immunization regimen, the poor immunogenicity may result from the unstable feature of BaMV. Nevertheless, the α-GalCer analogs, especially 7DW8-5 cooperated well with GH-DT to induce mouse immune response.

Figure 6:
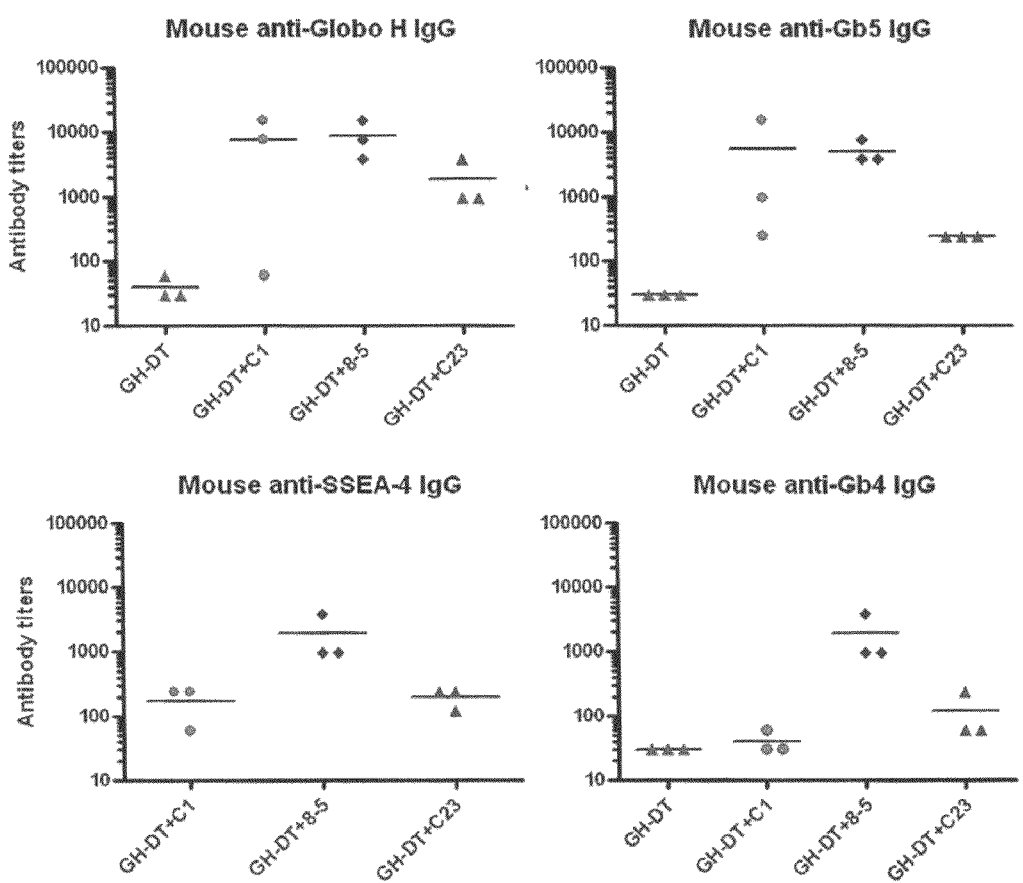
FIG. 6 shows fine specificity of mouse polyclonal antibody (anti-Globo H, anti-Gb5, anti-SSEA-4 and anti-Gb4) after vaccination. Mice sera were obtained two weeks after the $3^{rd}$ vaccination of 1.6 µg GH-DT with or without 2 µg of adjuvant. (Female, Balb/c, i.m.) The IgG titers were analyzed by glycan microarray and defined as the highest dilution yielding the MFI greater than 1000 (10 folds over background), PMT 400. Each spot presents as individual mouse titer.

Interestingly, the mouse polyclonal IgG antibodies generated by GH-DT and various glycolipid adjuvants not only neutralize Globo H but also cross-react with Gb5, SSEA-4 and Gb4 and C34 appears to be the most effective glycolipid adjuvant (FIG. 6). In order to search for a new composition of vaccine that can induce much higher titer of IgG than IgM, Globo H-DT conjugate and glycolipid C1 or C34 or commercially available adjuvant $AlPO_4$ (aluminium phosphate) or MF59 were tested.

Figure 7:
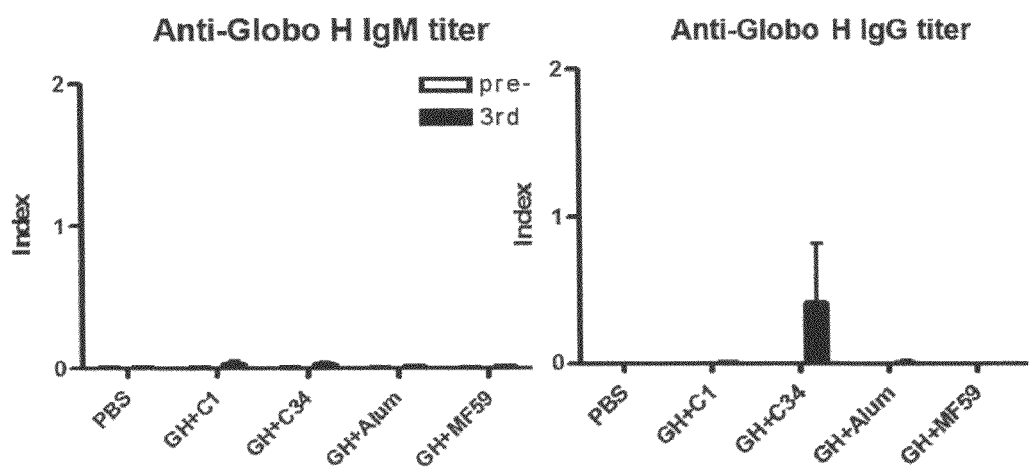
FIG. 7 shows IgM vs IgG antibody titers of Globo H-DT with different adjuvants.

Surprisingly, Globo H-DT with glycolipid C34 induces IgG antibody almost exclusively after the $3^{rd}$ vaccination (FIG. 7). To summarize, the novel glycolipid adjuvant 7DW8-5 combined with GH-DT conjugates was able to enhance both anti-Globo H IgG and IgM antibodies, and glycolipid adjuvant C34 combined with GH-DT can induce antibody titer of IgG much higher than IgM. They also exhibited diverse binding affinity to SSEA-3 (Gb5) and SSEA-4 antigens, both specifically expressed on the surface of breast cancer stem cells.

Figure 8:
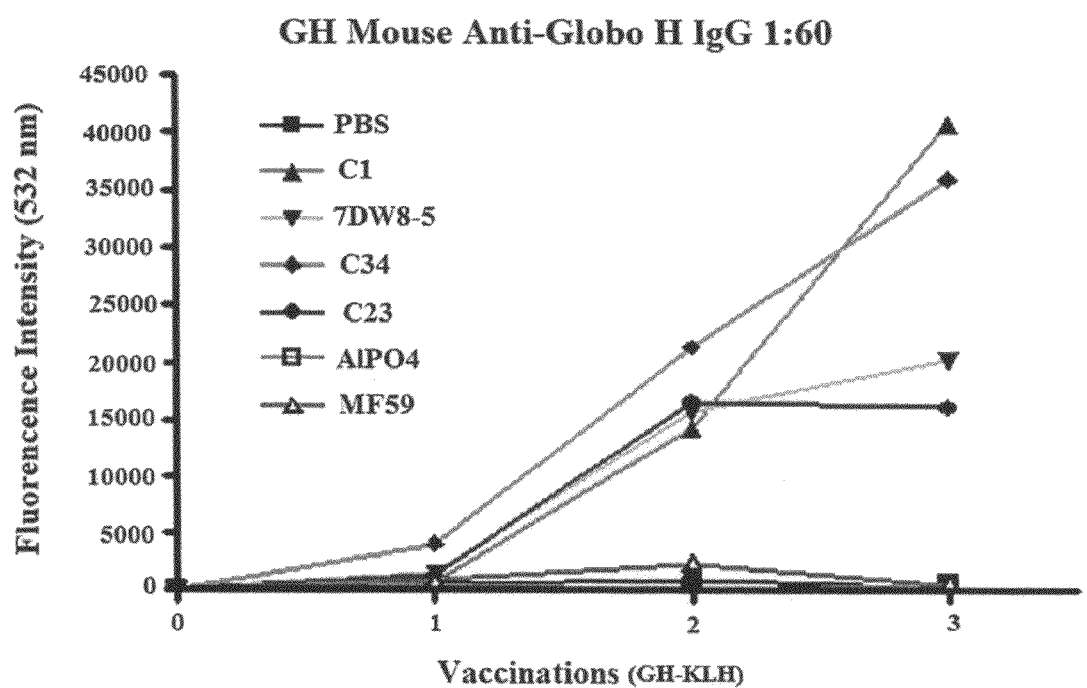
FIG. 8 shows evaluation of the adjuvant activities with GH-KLH vaccines. Female Balb/c mice were vaccinated i.m. with 1.6 µg GH-KLH and 2 µg indicated adjuvants and bled every two weeks after vaccination. The sera were diluted and introduced to microarray analysis.

In order to further compare the effect of different glycolipid adjuvants on Globo H vaccine, we immunized seven groups of mice with GH-KLH. The results suggested that mice vaccinated with glycolipids induced higher levels of anti-Globo H antibodies (FIG. 8). Although MF59 is a strong adjuvant it failed to collaborate with GH-KLH to induce antibodies against Globo H. $AlPO_4$ (aluminium phosphate) also showed no obvious impact on the induction of antibodies. On the other hand, GH-KLH along with C34 showed superior immunogenicity after the first and second vaccinations but exhibited no significant difference to C1 after the third vaccination. Overall, these findings suggest the potential of novel glycolipid derivatives as adjuvants for carbohydrate based vaccines.

Figure 9:
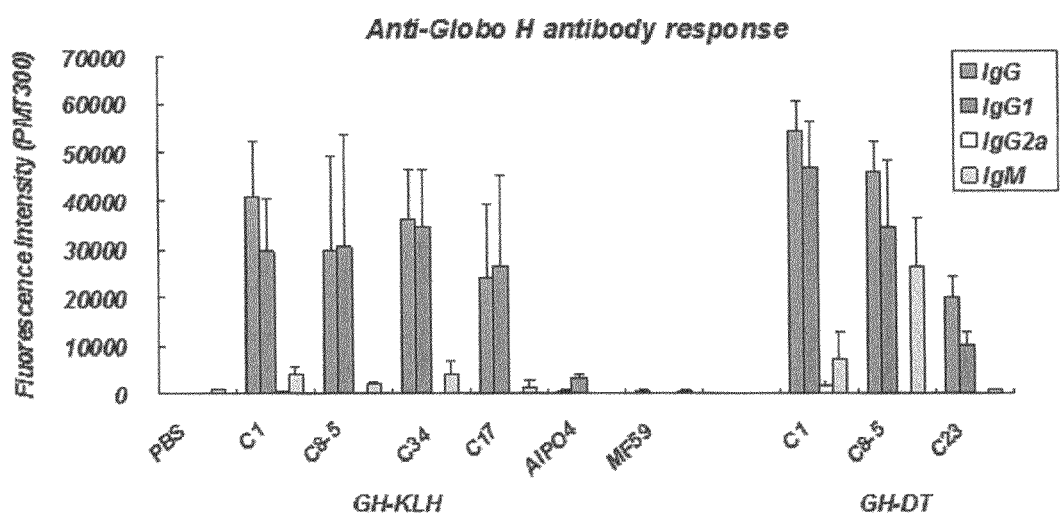
FIG. 9 shows antibody isotype profile after immunizations. Mice were vaccinated as described. Sera (1:60 dilutions) were introduced to microarray for antibody subclasses analysis (532 nm, PMT 300). Data presents as mean fluorescence of three mice±the SEM.

The nature of cellular and humoral immune response is influenced not only by antigen and adjuvant combinations but also by the carrier and route of immunization. As Sesardic and co-workers described, DT-CRM197, a mutant toxin devoid of toxic activity induces antigen-specific T cell proliferation and elevates splenocyte production of IL-2, IFN-γ and IL-6, suggesting its role in Th1 driven pathway. (Miyaji E N et al. (2001) *Infect Immun* 69:869-874; Godefroy S, et al. (2005) *Infect Immun* 73:4803-4809; Stickings P, et al. (2008) *Infect Immun* 76:1766-1773.) Despite the fact that the cytokine profile was predominantly Th1, subclasses of anti-CRM197 antibodies were IgG1 with no detectable IgG2a, which suggests a mixed Th1/Th2 response. These results prompted the evaluation of the antibody isotype profile of the Globo H vaccines, and present studies showed that GH-DT or GH-KLH in combination with glycolipid adjuvants induced mainly IgG1 antibody with a trace amount of IgG2a (FIG. 9).

Despite the fact that glycolipid adjuvants enhanced Th1 biased cytokines secretion when administrated alone intravenously (i.v.), the antibody class switch (IgG2a) was not observed. Overall, the glycolipids play a pivotal role in enhancing both cellular and humoral immune response.

Globo H, SSEA-3 and SSEA-4 Cancer Vaccines

Figure 10:
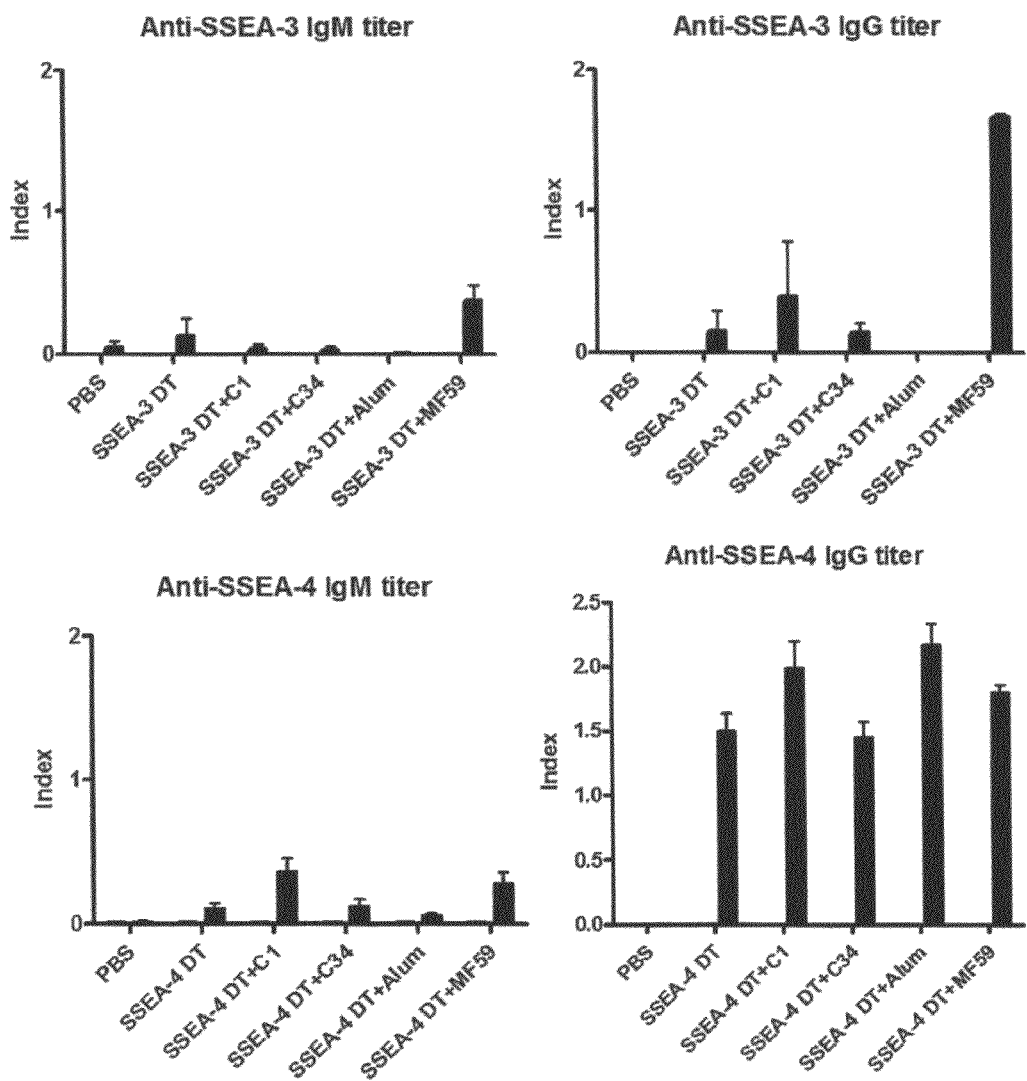
FIG. 10 shows antibody titers of IgM vs IgG induced by SSEA-3-DT or SSEA-4-DT with different kind of glycolipid adjuvants.

SSEA-3 (Gb5) and SSEA-4 conjugated with DT were synthesized and tested. After $3^{rd}$ vaccination, antibodies titer of IgM and IgG were compared and it was found that SSEA-3-DT and SSEA-4-DT also induced much higher titer of IgG than IgM (FIG. 10).

Figure 11:
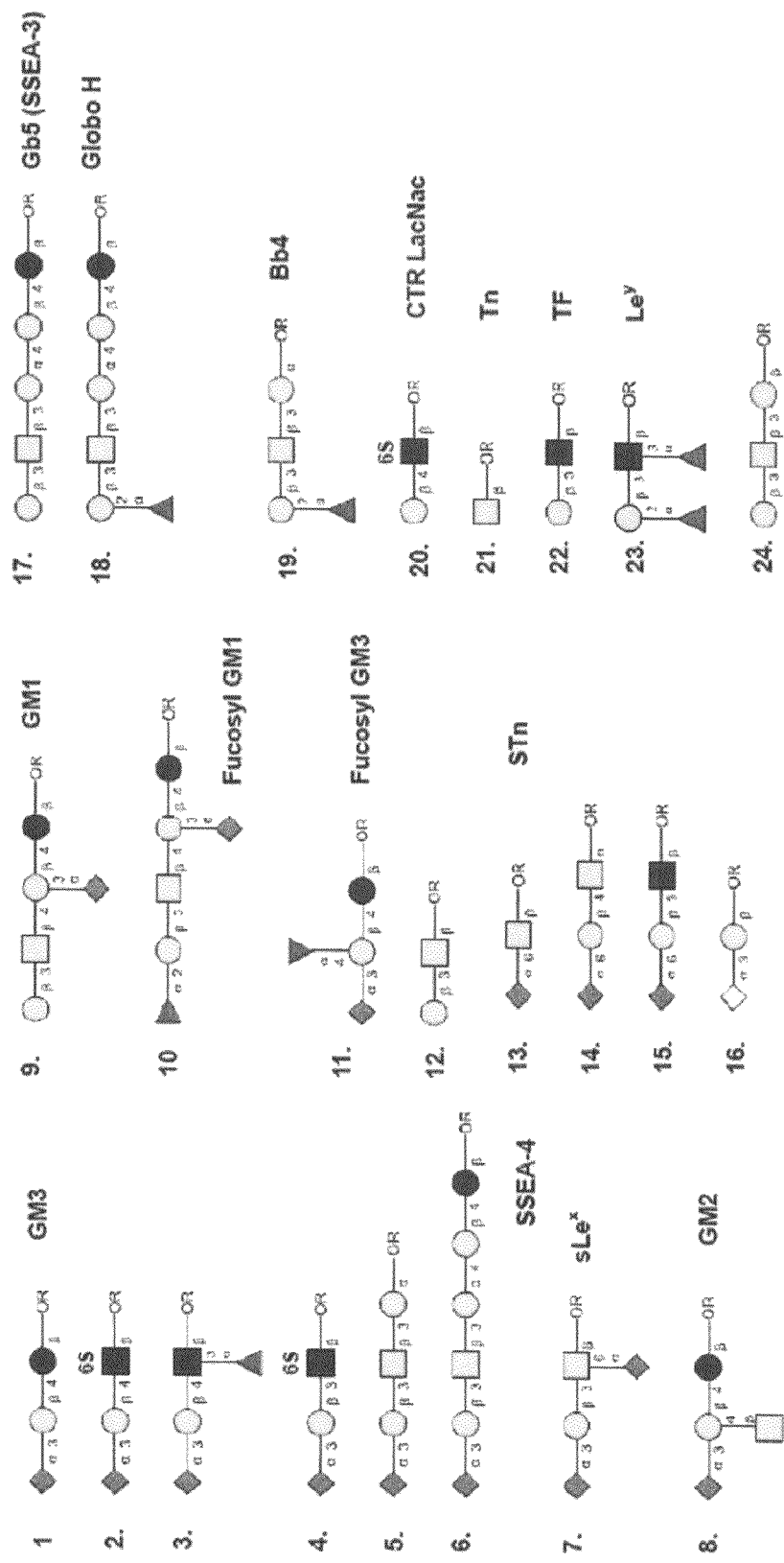
FIG. 11 shows structures of 24 glycans on the cell surface.

Since GH-DT and C34 induced antibodies to recognize Globo H, Gb5 and SSEA-4, the specificity of SSEA-3-DT and SSEA-4-DT vaccines in the presence of adjuvants using an array of 24 glycans were examined with focus on the study of IgG (FIG. 11).

Figure 12A:
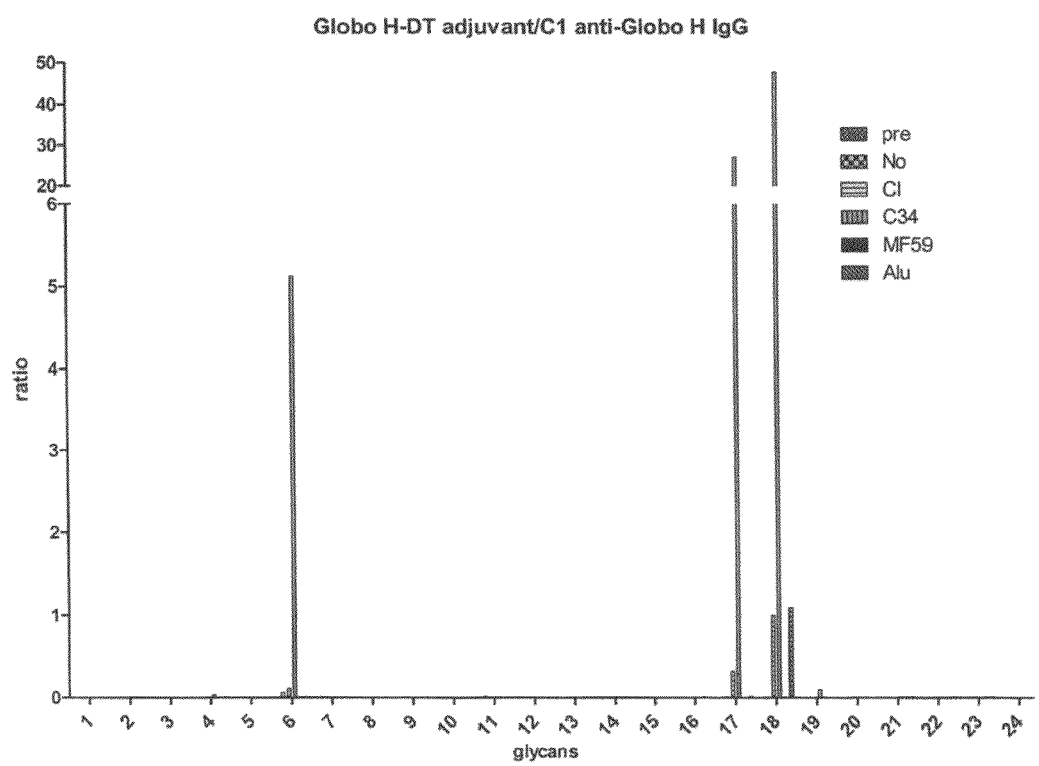
FIGS. 12A-12C show cross-reactivity studies of induced IgG by different vaccines.
Figure 12B:
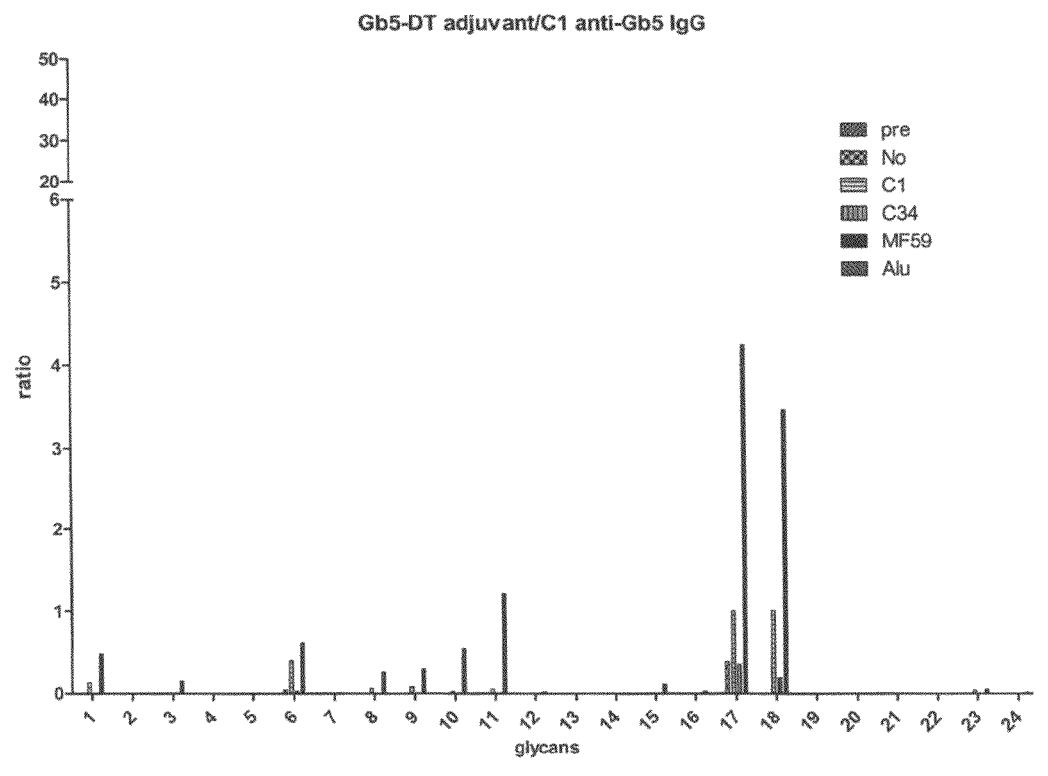
Figure 12:
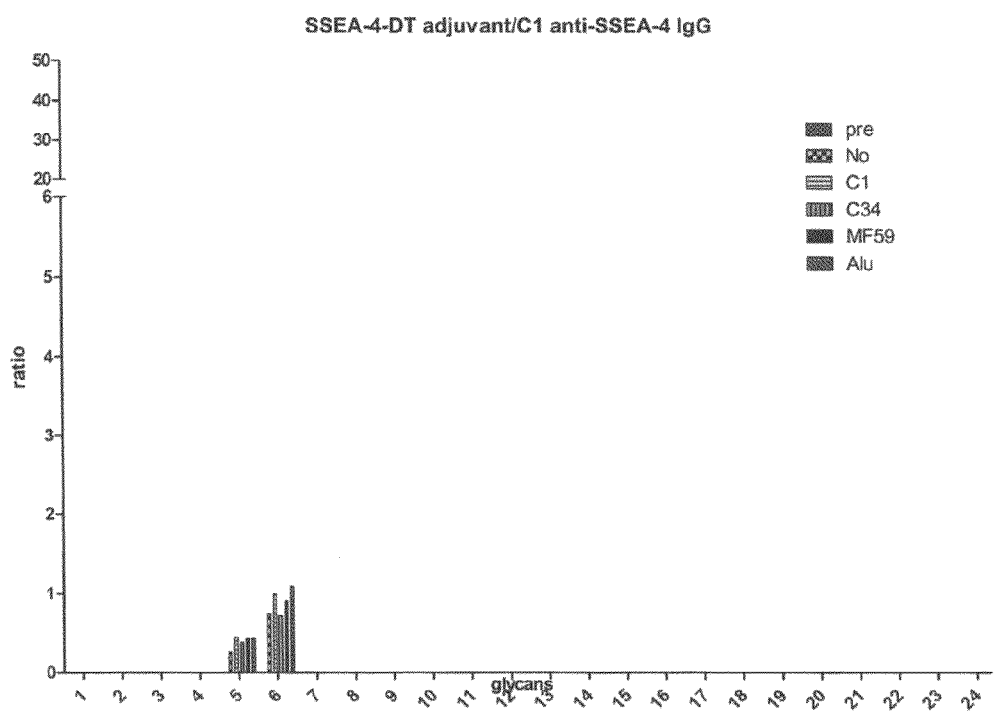

As shown in FIG. 12, mice immunized with Globo H-DT and C34 adjuvant induced antibodies that can recognize Globo H, SSEA-3 (Gb5) and SSEA-4 with high selectivity, and vaccine SSEA-3-DT with adjuvant MF59 induced high immune response with low selectivity. On the other hand, SSEA-3-DT combined with adjuvant C34 only induced antibodies against Globo H, SSEA-3, and SSEA-4.

Interestingly, SSEA-4-DT (sialyl-Gb5) in the presence or absence of adjuvants induced IgG and IgM antibodies specifically recognizing SSEA-4 and its truncated structures (SSEA-4 with head lactose deletion). Without being bound by theory, it is postulated that sialic acid is highly immunogenic and induces highly specific immune response.

Immunization of mice with SSEA-3-DT-C34 induced antibodies reactive with Globo H, SSEA-3 and SSEA-4, suggesting that a Globo H-based vaccine can target tumor cells and breast cancer stem cells expressing Globo H, SSEA-3 and SSEA-4.

Immunization of mice with Globo H-DT-C34 induced antibodies reactive with Globo H, SSEA-3 and SSEA-4, suggesting that a Globo H-based vaccine can target tumor cells and breast cancer stem cells expressing Globo H, SSEA-3 and SSEA-4.

Immunization of mice with SSEA-4-DT induced antibodies reactive with SSEA-4, suggesting that a SSEA-4-DT-based vaccine can target tumor cells and breast cancer stem cells expressing SSEA-4.

Tumor Size Reduction by Cancer Vaccines

Figure 13:
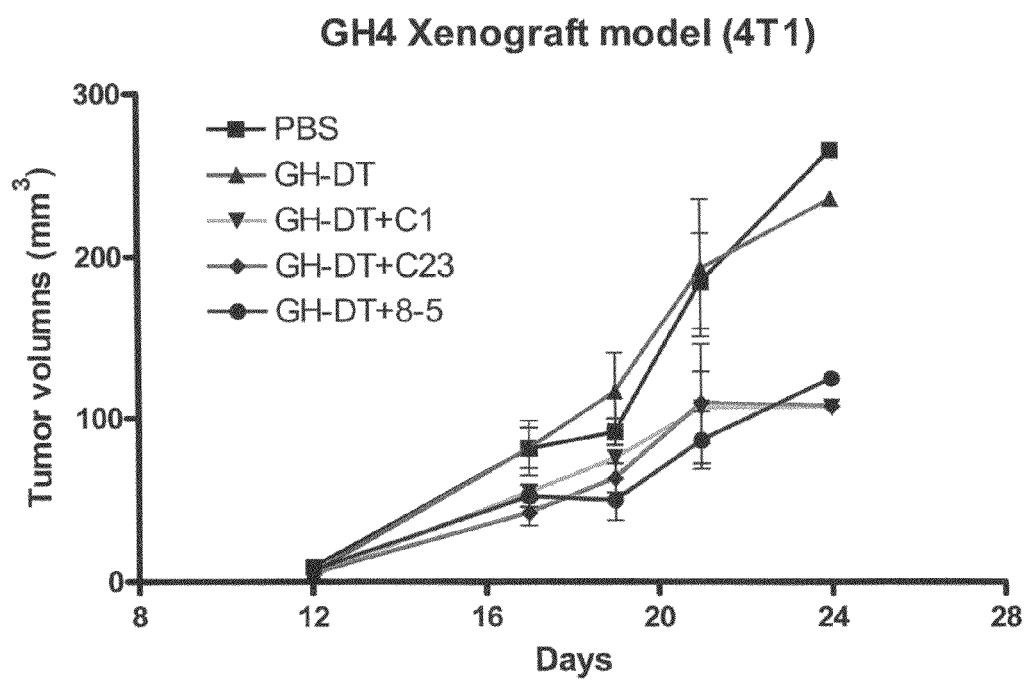
FIG. 13 shows a mouse xenograft model. $2 \times 10^5$ 4T1 mouse metastatic mammary tumor cells were prepared in sterile PBS and injected subcutaneously to vaccinated Balb/c mice. Mouse tumor size was measured by Vernier caliper and defined as (length×width×width)/2 ($mm^3$)

In order to directly assess the efficacy of the synthetic glycoconjugate vaccines, the tumor sizes were measured three times per week as shown in FIG. 13. In general, tumor grows 2 weeks after injection with 4T1, a Globo H bearing breast cancer cell line. All the vaccinated groups along with glycolipid adjuvants still showed comparative smaller tumor progression compared to GH-DT alone and PBS control at day 24. The data suggest that vaccination with GH-DT and a glycolipid adjuvant delayed some degree of the tumor progression in vivo.

Expression of SSEA-3 and SSEA-4 in Breast Cancer and BCSCs

The expression of Globo H in BCSCs, but at a lower frequency than non-BCSCs, and a higher frequency of SSEA-3 expression than Globo H expression in breast cancer and BCSCs has been shown. (Chang W-W. et al., (2008) *Proc*

Natl Acad Sci USA 105(33):11667-11672, incorporated herein by reference in its entirety.)

The clinical characteristics of 35 patients with breast cancer in whom range of SSEA-3 or SSEA-4 expression was measured, are summarized in Table 2. The median age was 48 years (ranging from 31 to 82 years). They consisted of 1 stage 0, 10 stage I, 19 stage II, and 5 stage III. A majority of the tumor specimens had the pathology of infiltrating ductal carcinoma (80.0%), with 51.4% positive for ER and 65.7% positive for node involvement. In Table 2, the ranges of SSEA-3 or SSEA-4 expression is represented by the percentage of positive cells within total cancer cells. A t test was used for statistical analysis of SSEA-3 or SSEA-4 expression relative to HER-2 or nodal involvement status. HER-2 expression was determined by immunohistochemistry. There was no significant correlation between expression level of SSEA-3 or SSEA-4 on tumors and various clinico-pathological factors, such as stage (SSEA-4: P=0.3498; SSEA-3: P=0.9311), or HER-2 (SSEA-4: P=0.0142; SSEA-3: P=0.0128) (Table 2).

BCSCs were defined as the remaining populations of CD45$^-$ cells. Range was calculated as percentage of positive cells in total cells.

As summarized in Table 3, among the 27/35 (77.1%) samples expressing SSEA-3, the percentage of positive cells ranged from 1.4% to 66.4%. The non-BCSCs isolated from 25/35 tumors expressed SSEA-3, with the percentage of positive cells ranging from 24.3% to 70.4%. In comparison, BCSCs from 23 of 35 (65.7%) tumors showed positive staining for SSEA-3, with the percentage of positive cells ranging from 5.0% to 58.4%.

Among the 34/35 (97.1%) samples expressing SSEA-4, the percentage of positive cells ranged from 0.5% to 77.1%. The non-BCSCs isolated from 32/35 tumors expressed SSEA-4, with the percentage of positive cells ranging from 24.0% to 78.1%. In comparison, BCSCs from 31 of 35 (88.6%) tumors showed positive staining for SSEA-4, with the percentage of positive cells ranging from 5.6% to 83.6%.

TABLE 2

Clinical characteristics of patients with breast cancer.

| Characteristic | No. | % | SSEA4 Percent cells with expression Median (range) | P value | SSEA3 Percent cells with expression Median (range) | P value |
|---|---|---|---|---|---|---|
| Patients enrolled | 35 | 100 | | | | |
| Age, years | | | | | | |
| Median | 48 | | | | | |
| Range | 31-82 | | | | | |
| Tumor type | | | | | | |
| Infiltrating ductal carcinoma | 28 | 80.0 | | | | |
| Infiltrating lobular carcinoma | 1 | 2.8 | | | | |
| Ductal carcinoma in situ | 1 | 2.8 | | | | |
| Medullary carcinoma | 1 | 2.8 | | | | |
| Atypical medullary carcinoma | 1 | 2.8 | | | | |
| Metaplastic carcinoma | 2 | 6.0 | | | | |
| Inflammatory carcinoma | 1 | 2.8 | | | | |
| Stage | | | | 0.7880 | | 0.9311 |
| 0 | 1 | 2.9 | 33.1 (33.1) | | 1.4 (1.4) | |
| I | 10 | 28.6 | 41.4 (0.5-69.1) | | 36.4 (0.0-55.9) | |
| II | 19 | 54.3 | 39.3 (0.0-77.1) | | 30.9 (0.0-66.4) | |
| III | 5 | 14.2 | 49.8 (7.7-70.7) | | 32.3 (0.0-36.1) | |
| Node involvement | | | | 0.0322 | | 0.4925 |
| Negative | 23 | 65.7 | 37.8 (0.0-69.1) | | 30.9 (0.0-66.4) | |
| Positive | 12 | 34.3 | 49.1 (17.4-77.1) | | 35.8 (0.0-60.7) | |
| ER | | | | 0.0142 | | 0.0128 |
| Negative | 18 | 51.4 | 36.2 (0.5-60.3) | | 29.7 (0.0-38.6) | |
| Positive | 17 | 48.6 | 48.5 (0.0-77.1) | | 40.0 (0.0-66.4) | |

Primary tumor cells isolated from enrolled patients by enzymatic digestion were stained with specific antibodies to CD45, CD24, CD44, and CD45$^+$ cells were first gated out to eliminate the leukocytes. To compare the SSEA-3 or SSEA-4 expression between BCSCs and non-BCSCs, CD45$^-$ tumor cells were further separated into BCSCs and non-BCSCs based on their expressions of surface markers. The BCSCs were identified as CD45$^-$/CD24$^-$/CD44$^+$ cells; the rest of the CD45$^-$ population were considered as non-BCSCs.

Using this approach, the expression of SSEA-3 or SSEA-4 in BCSCs and non-BCSCs were evaluated in 35 tumor specimens. Overall, SSEA-4 was detected in 34/35 (97.1%) and SSEA-3 in 27/35 (77.1%) of the tumors (Table 3). SSEA4 or SSEA3 expression was determined by flow cytometry. BCSCs were defined as CD45$^-$CD24$^-$CD44$^+$ cells and non-

TABLE 3

Comparison of SSEA4 and SSEA3 expression in BCSCs and non-BCSCs

| Glycan Population | No. of patients | Positive No. | percent Cells with expression median (Range) | % of Total |
|---|---|---|---|---|
| SSEA-4 | | | | |
| Total | 35 | 34 | 41.4 (0.5-77.1) | 97.1 |
| Non-BCSCs | 35 | 32 | 43.7 (4.0-78.1) | 91.4 |
| BCSCs | 35 | 31 | 37.1 (5.6-83.6) | 88.6 |

TABLE 3-continued

Comparison of SSEA4 and SSEA3
expression in BCSCs and non-BCSCs

| Glycan Population | No. of patients | Positive No. | percent Cells with expression median (Range) | % of Total |
|---|---|---|---|---|
| SSEA-3 | | | | |
| Total | 35 | 27 | 36.4 (1.4-66.4) | 77.1 |
| Non-BCSCs | 35 | 25 | 40.5 (24.3-70.4) | 71.4 |
| BCSCs | 35 | 23 | 24.3 (5.0-58.4) | 65.7 |

Expression of SSEA-4 in BCSCs

Figure 15:
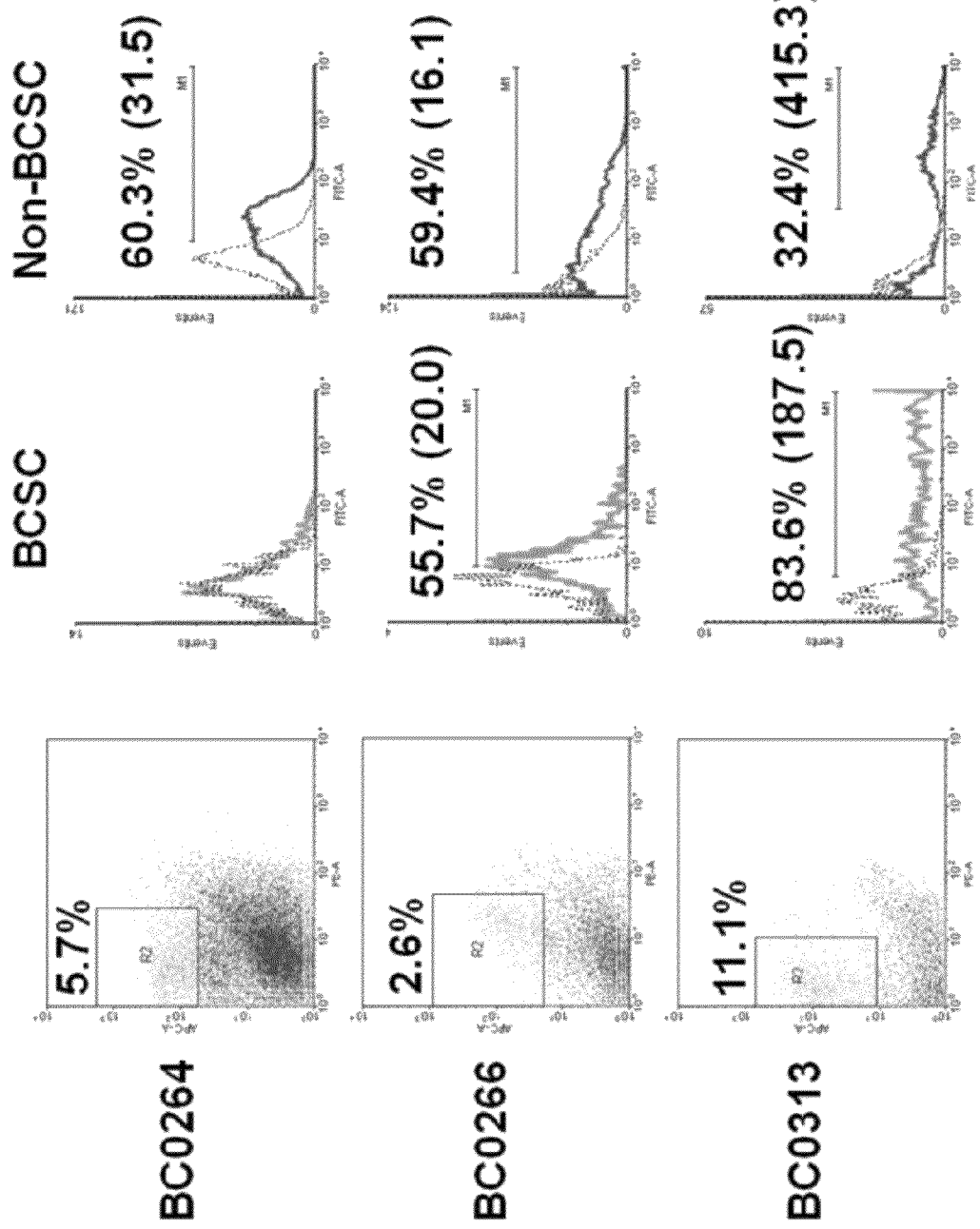
FIG. 15 shows flow cytometric analysis of SSEA-4 expression in primary breast cancer stem cells. Expression of SSEA-4 on the surface of BCSCs and non-BCSCs was evaluated with four-color immunofluorescence staining and subsequent flow cytometric analysis. BCSCs were defined as $CD45^-/CD24^-/CD44^+$ cells, and non-BCSCs were defined as other populations of $CD45^-$ cells, as shown in left panel. Expression of antigens of interest on BCSCs and non-BCSCs is shown in the middle and right panel, respectively. The dotted line represents isotype control, and the numbers represent the percentage of positive cells.

To compare the SSEA-4 expression between BCSCs and non-BCSCs, CD45⁻ tumor cells were further separated into BCSCs and non-BCSCs based on their expressions of surface markers. The BCSCs were identified as CD45⁻/CD24⁻/CD44⁺ cells; the rest of the CD45⁻ population were considered as non-BCSCs. The expression of SSEA-4 within each of these two gated populations varied among tumor samples a shown in FIG. 15. For instance, BCSCs of patient BC0264, which accounted for 5.7% of the total isolated tumor cells, were negative for SSEA-4, whereas 60.3% of the non-BCSCs expressed SSEA-4. For patient BC0266, SSEA-4 expression was detected in 59.4% of non-BCSCs and 55.7% of BCSCs. For patient BC0313, SSEA-4 expression was detected in 32.4% of non-BCSCs and 83.6% of BCSCs. Altogether, SSEA-4 was detected in 34/35 (97.1%) samples tested with the percentage of positive cells ranging from 0.5% to 77.1%). (Table 32).

Expression of SSEA-3 and SSEA-4 in Normal Tissues

Using tissue microarray, SSEA-4 expression was analyzed among 20 different organs by immunohistochemical staining, as shown in Table 4 (E, epithelial; C, connective tissue).

TABLE 4

Expression of SSEA-4 in normal tissues

| Normal tissue | Antigen SSEA4 | |
|---|---|---|
| Brain | 0/5 | |
| Bone | 0/5 | |
| Lymph node | 0/5 | |
| | E | C |
| Breast | 1/5 | 0/5 |
| Colon* | 2/4 | 0/4 |
| Esophagus | 0/5 | 0/5 |
| Intestine | 5/5 | 0/5 |
| Kidney | 2/5 | 0/5 |
| Liver | 0/5 | 0/5 |
| Lung | 1/5 | 0/5 |
| Ovary | 1/5 | 0/5 |
| Pancreas | 1/5 | 0/5 |
| Prostate | 0/5 | 0/5 |
| Rectum | 5/5 | 0/5 |
| Skin | 0/5 | 0/5 |
| Spleen | 0/5 | 0/5 |
| Stomach | 4/5 | 0/5 |
| Testis | 4/5 | 0/5 |
| Thymus gland | 1/5 | 0/5 |
| Uterine cervix | 1/5 | 0/5 |

Figure 16:
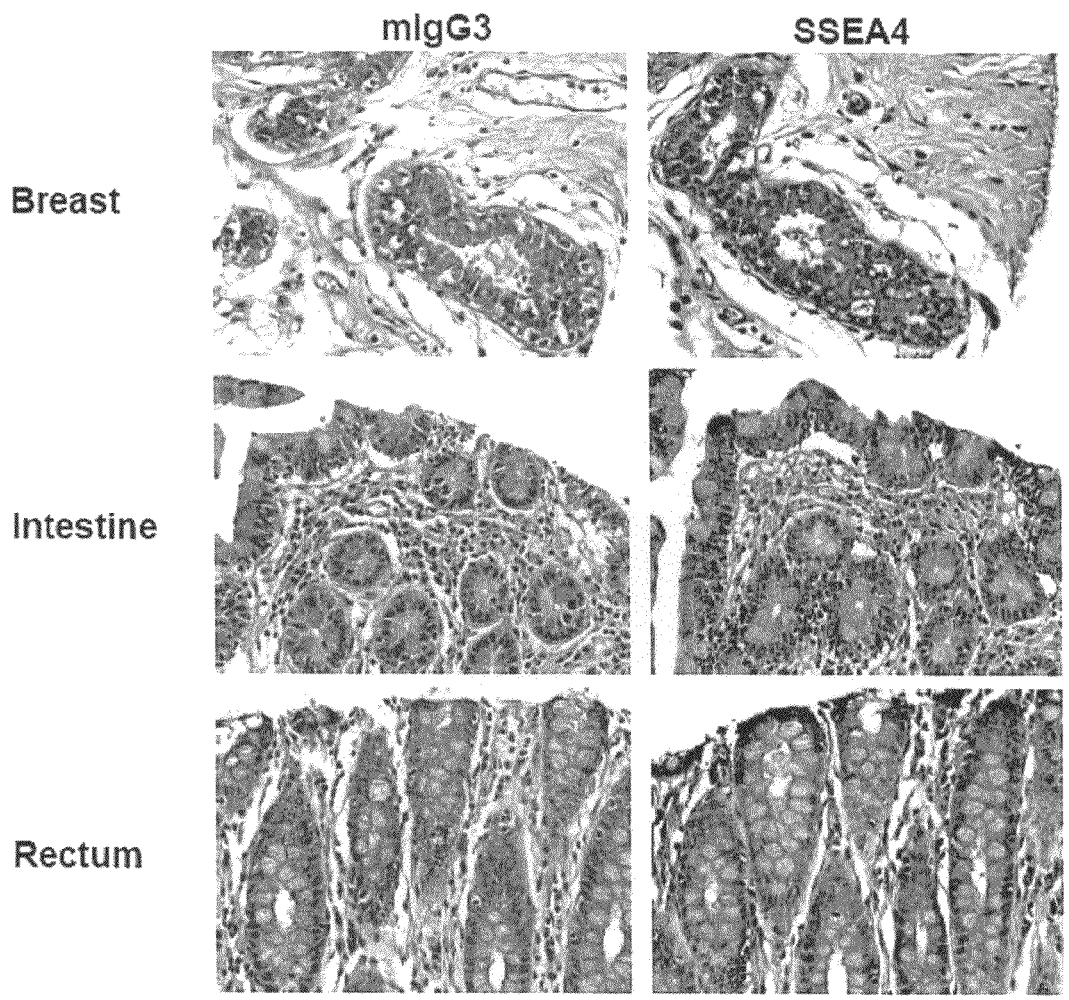
FIG. 16 shows restricted expression of SSEA-4 in normal tissues. Immunohistochemical staining of normal tissue arrays was used to examine the expression of SSEA-4 in breast, small intestine, and rectum. Positive staining for SSEA-4 was restricted to the apical surface of epithelial cells.

SSEA-4 is expressed on the epithelial cells of several glandular tissues, such as breast, colon, gastrointestinal tract, kidney, lung, ovary, pancreas, rectum, stomach, testes, thymus and uterine cervix (Table 4). Further, in a manner similar to Globo H and SSEA-3 (Chang W-W. et al., (2008) *Proc Natl Acad Sci USA* 105(33):11667-11672), SSEA-4 expression was confined mainly to the cytoplasm or apical surface of epithelial cells which were essentially inaccessible to the immune system, as shown in FIG. 16.

By comparison, Globo H is expressed on the epithelial cells of several glandular tissues, such as breast, gastrointestinal tract, pancreas, prostate, and uterine cervix. The distribution of SSEA3 is similar to that of Globo H except for its absence in normal breast tissues but presence in kidney, rectum, testis, and thymus, which were negative for Globo H (Chang W-W. et al., (2008) *Proc Natl Acad Sci USA* 105(33): 11667-11672).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

General Methods, Materials and Instrumentation

Materials

Commercial solvents and reagents were used as received without further purification and purchased from Sigma-Aldrich, Acros, Merck, Echo chemical and Senn Chemical. Monoclonal antibody Mbr1 was purchased from ALEXIS biochemicals, Cy3-conjugated anti-mouse IgG (IgG, IgG1, and IgG2a) and IgM antibodies were from Jackson Immuno Research. DT-CRM197 Protein and Tetanus toxoid were purchased from Merck and Adimmune, respectively. Aluminium phosphate gel adjuvant ($AlPO_4$) was purchased from Brenntag Biosector. Bamboo virus and VK9 monoclonal antibody were prepared from Dr. Lin's and Dr. Yu's laboratory, respectively. Glycolipid derivatives were synthesized and provided by Dr. Wong's laboratory.

General Methods

Molecular sieves (MS, AW-300) used in glycosylations were crushed and activated before use. Reactions were monitored with analytical TLC plates (PLC silica gel-60, $F_{254}$, 2 mm, Merck) and visualized under UV (254 nm) or by staining with p-anisaldehyde. Flash column chromatography was performed on silica gel (40-63 μm) or LiChroprep RP18 (40-63 μm). Dialysis membrane (Cellulose Ester, MCCO=10,000) was washed by dd$H_2O$ before use.

Instrumentation

Proton nuclear magnetic resonance ($^1H$ NMR) spectra, carbon nuclear magnetic resonance ($^{13}C$ NMR) spectra were recorded by Bruker Advance 600 (600 MHz/150 MHz) NMR spectrometers. Chemical shifts for protons are reported in ppm (δ scale) and referenced to tetramethylsilane (δ=0). Chemical shifts for carbon are also reported in parts per million (ppm, δ scale). DEPT 135 (Distortion-less enhancement by polarization transfer) was employed for determination of multiplicity. Data are represented as follows: chemical shift, multiplicity (s=singlet, d=doublet, t=triplet, q=quartet, m=multiplet, br=broad), integration and coupling constant (J) in Hz. High resolution mass spectra were obtained by BioTOF III, and the MALDI-TOF MS were employed by Ultraflex II TOF/TOF200.

Example 1

Synthesis of Globo H Conjugated with Different Carrier Proteins

Globo H (1; see FIG. 11) and its fragments 2-10 were synthesized by using a programmable one-pot strategy. (Huang C-Y, et al. (2006) *Proc Natl Acad Sci USA* 103:15-20.) The reaction of 1 was carried with an efficient homobifunctional linker in anhydrous DMF solution at room temperature. (Wu X, et al. (2004) *Org Lett* 6:4407-4410; Wu X, Bundle D R (2005) *J Org Chem* 70:7381-7388.) The reaction was readily monitored by TLC. Once the disappearance of the free amine with a larger $R_f$ product occurred, the reaction mixture was evaporated to remove DMF, and washed with dichloromethane and water to remove the excess amount of linker. Finally, the product was purified by reverse phase (C18) column chromatography, and gradually eluted with water containing 1% acetic acid to 40% methanol in water. The solution was then lyphophilized to yield the light yellow product 12. Finally, for protein conjugation, the purified Globo H half ester 12 (30-40 equiv) was incubated with individual carrier proteins in phosphate buffer (10 mM, pH 7.2) for 24 hours at room temperature (FIG. 14). Importantly, the protein concentration must be adjusted to ~5 mg/mL to maximize the coupling of lysine residues with Globo H half ester. After 24 h, the glycoconjugates were then diluted, and dialyzed against deionized water to remove the remaining of p-nitrophenyl group. The solution was then lyphophilized to a white powder to give 13, 14, and 15.

The Globo H-protein conjugates were characterized by MALDI-TOF analysis to determine the number of Globo H molecules on each carrier protein. The average number of Globo H incorporation is listed in Table 1 shown supra.

The glycoconjugates 13, 14, 15 were dissolved in ddH$_2$O to yield a final concentration around 1 pmol/μL. Sinapinic acid was selected as a matrix and mixed with freshly prepared acetonitrile and deionized water (1:1 v/v) to make the final matrix concentration in 10 mg/mL including 0.1% TFA. Each sample was detected under a linear positive mode to get the m/z spectrum. The molecular weight of each glycoconjugate was determined by m/z. The glycoconjugate 14 showed heterogeneity, indicating an average of 2~4 incorporations. The GH-KLH conjugate showed the greatest number of Globo H incorporation, mostly due to the larger size and more Lys residues of KLH. The same coupling procedure using p-nitrophenyl linker was also applied to bamboo mosaic virus which contains more than 100,000 lysine residues on the coat of virus. However, the instability of the virus while reacting in sodium phosphate buffer (pH=7.2) at 4° C. is a major concern for further development. Additionally, the GH-BaMV 16 limits its detection by MALDI-TOF analysis due to its tremendous size. Finally, the lyphophilized glycoconjugates were stored at −30° C. and reconstituted with sterile water before immunization.

Example 2

Glycan Microarray Fabrication and Validation

The synthetic Globo H and truncated fragments (FIG. 1) were attached with a pentylamine linker at the reducing ends and covalently immobilized onto the NHS-coated glass slide. Nine of the eleven oligosaccharides were selected to be printed on the microarray. Serial oligosaccharide concentrations (1, 5, 10, 20, 40, 50, 80, 100 μM) were tested to optimize the binding affinity and fluorescence intensity. Each microarray slide was spotted with 50 μM of nine Globo H analogs (SSEA-4, GH, Gb5, Gb4, Gb3, Gb2, BB4, BB3, and BB2) respectively in 12 replications. After reaction in 80% humidity atmosphere, the slides were stored at room temperature in desiccators before use.

To validate the carbohydrates on the microarray, mouse monoclonal antibodies (VK9 and Mbr1 for Globo H, and anti-SSEA-3) and respective secondary antibodies (goat anti-mouse IgG and IgM) were used to examine the binding specificity, and the results are shown in FIGS. 2A-2C. The data suggests that VK9 and Mbr1 both recognized Globo H and the outer tetrasaccharide BB4, although MBr1 also slightly recognized BB3. (Gilewski T et al. (2001) *Proc Natl Acad Sci USA* 98:3270-3275; Huang C-Y, et al. (2006) *Proc Natl Acad Sci USA* 103:15-20.) In addition, anti-SSEA-3 antibody specifically recognized SSEA-3 antigen (Gb5) without any cross reactivity. The results indicated that the Globo H microarray could be employed to profile the specificity and potency of polyclonal antibodies from immunized mice.

Example 3

Mouse Immunization

In this study, a group of mice was immunized with 1 μg synthetic Globo H (GH)-conjugates with or without the glycolipid adjuvant, α-GalCer (C1) subcutaneously. Ten days after three vaccinations at weekly intervals, mice sera were collected and subsequently introduced to the glycan microarray to evaluate the antibody levels. It was found that GH-KLH, GH-DT and GH-BV are the most effective immunogens for IgM induction, followed by GH-TT, and GH-BSA as summarized in FIG. 3A, and α-GalCer is capable of stimulating the immune response to induce high levels of IgM antibodies. A similar trend was also observed in mouse IgG antibodies (FIG. 3B), and the relative IgG levels were higher than IgM levels. In brief, despite the lower carbohydrate density of the synthetic glycoconjugate, GH-DT exhibited a similar immunogenicity to GH-KLH, and the adjuvant α-GalCer was shown to enhance the immune response.

Since C1 was shown to be an effective adjuvant for GH-DT, other glycolipids with better adjuvant activity than C1 were examined as shown in FIG. 4. (Fujio M, et al. (2006) *J Am Chem Soc* 128:9022-9023.)

Groups of mice were immunized intramuscularly with 1.6 μg of GH-DT and GH-BV with or without 2 μg of glycolipids twice a week. Sera were obtained two weeks after the third vaccination and introduced to glycan microarray analysis. In general, mouse anti-Globo H IgG titers increased as immunization proceeded but the IgM levels were almost independent of vaccination times (FIG. 5). Among the GH-BV vaccinated groups, there was no significant difference in the IgM level between glycolipid-vaccine treatment and the vaccine alone. Although the results suggested that GH-BV in combination with glycolipid was not an effective immunization regimen, the poor immunogenicity may result from the unstable feature of BaMV. Nevertheless, the α-GalCer analogs, especially 7DW8-5 cooperated well with GH-DT to induce mouse immune response.

Interestingly, the mouse polyclonal IgG antibodies generated by GH-DT and various glycolipid adjuvants not only neutralize Globo H but also cross-react with Gb5, SSEA-4 and Gb4 and C34 appears to be the most effective (FIG. 6). In order to search for a new composition of vaccine that can induce much higher titer of IgG than IgM, Globo H-DT conjugate and glycolipid C1 or C34 and commercially available adjuvant AlPO$_4$ (aluminium phosphate) or MF59 were tested. Surprisingly, Globo H-DT with glycolipid C34 can induce almost IgG antibody after 3$^{rd}$ vaccination (FIG. 7). In summary, the novel glycolipid adjuvant 7DW8-5 combined with GH-DT conjugates was able to enhance both anti-Globo H IgG and IgM antibodies, and glycolipid adjuvant C34 combined with GH-DT can induce antibody titer of IgG much higher than IgM. They also exhibited diverse binding affinity to Gb5 and SSEA-4 antigens, both specifically expressed on the surface of breast cancer stem cells.

In order to further compare the effect of different glycolipid adjuvants on Globo H vaccine, seven groups of mice with GH-KLH. were immunized The results suggested that mice vaccinated with glycolipids induced higher levels of anti-Globo H antibodies (FIG. 8). Although MF59 is a strong adjuvant it failed to collaborate with GH-KLH to induce antibodies against Globo H. $AlPO_4$ (aluminium phosphate) also showed no obvious impact on the induction of antibodies. On the other hand, GH-KLH along with C34 showed superior immunogenicity after the first and second vaccinations but exhibited no significant difference to C1 after the third vaccination.

DT-CRM197, a mutant toxin devoid of toxic activity induces antigen-specific T cell proliferation and elevates splenocyte production of IL-2, IFN-γ and IL-6, suggesting its role in Th1 driven pathway. (Miyaji E N et al. (2001) *Infect Immun* 69:869-874; Godefroy S, et al. (2005) *Infect Immun* 73:4803-4809; Stickings P, et al. (2008) *Infect Immun* 76:1766-1773.) Despite the fact that the cytokine profile was predominantly Th1, subclasses of anti-CRM197 antibodies were IgG1 with no detectable IgG2a, which suggests a mixed Th1/Th2 response. These results prompted the evaluation of the antibody isotype profile of the Globo H vaccines, and present studies showed that GH-DT or GH-KLH in combination with glycolipid adjuvants induced mainly IgG1 antibody with a trace amount of IgG2a (FIG. 9).

Despite the fact that glycolipid adjuvants enhanced Th1 biased cytokines secretion when administrated alone intravenously (i.v.), the antibody class switch (IgG2a) was not observed. Overall, the glycolipids play a pivotal role in enhancing both cellular and humoral immune response.

Gb5 and SSEA-4 conjugated with DT were also synthesized by the same strategy. After $3^{rd}$ vaccination, antibodies titer of IgM and IgG were compared and it was found that Gb5-DT and SSEA-4-DT also induced much higher titer of IgG than IgM (FIG. 10).

Example 4

Specificity Studies of Antibodies Induced by Different Vaccine Composition

Since GH-DT and C34 induced antibodies to recognize Globo H, Gb5 (SSEA-3) and SSEA-4, the specificity of SSEA-3-DT and SSEA-4-DT vaccines in the presence of adjuvants using an array of 24 glycans with focus on the study of IgG were next examined (FIG. 11).

As shown in FIG. 12, mice immunized with Globo H-DT and C34 adjuvant induced antibodies that can recognize Globo H, SSEA-3 (Gb5) and SSEA-4 with high selectivity, and vaccine SSEA-3-DT with adjuvant MF59 induced high immune response with low selectivity. On the other hand, SSEA-3-DT combined with adjuvant C34 only induced antibodies against Globo H, SSEA-3, and SSEA-4.

Interestingly, SSEA-4-DT in the presence or absence of adjuvants induced IgG and IgM antibodies specifically recognizing SSEA-4 and its truncated structures (SSEA-4 with head lactose deletion). It is however not clear about the origin of the selectivity.

In order to directly assess the efficacy of the synthetic glycoconjugate vaccines, the tumor sizes three times per week were measured as shown in FIG. 13. In general, tumor grows 2 weeks after injection with 4T1, a Globo H bearing breast cancer cell line. All the vaccinated groups along with glycolipid adjuvants still showed comparative smaller tumor progression compared to GH-DT alone and PBS control at day 24. The preliminary data suggested that vaccination with GH-DT and a glycolipid adjuvant indeed delayed some degree of the tumor progression in vivo.

Example 5

Preparation of Globo H Half Ester

The Globo H half ester was prepared as follows:

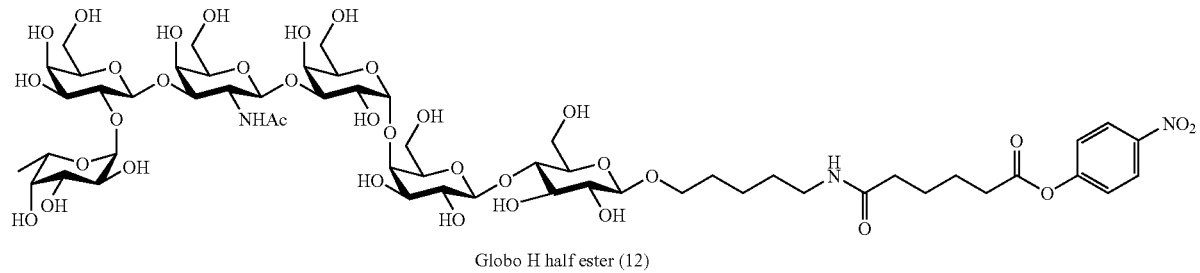

Globo H half ester (12)

Globo H amine 1 (5 mg, 4.54 μmol) was dissolved in anhydrous DMF solution. p-nitrophenyl ester linker (8.8 mg, 22.7 μmol) was then added and stirred for 1~3 hours at room temperature. The reaction was monitored by TLC (1% AcOH in methanol) and Ninhydrin test. The disappearance of free amine with a larger $R_f$ product indicated the completion of the reaction. The reaction mixture was evaporated under reduced pressure without heating to remove DMF, and then extracted with $CH_2Cl_2$ and water containing 1% of acetic acid twice. The water solution was concentrated and purified by reverse phase (C18) column chromatography, and gradually eluted with $H_2O$ containing 1% of acetic acid to $MeOH:H_2O=4:6$. The solution was then lyphophilized to a light yellow solid product 12 (5.4 mg, Yield 88%) $^1H$ NMR (600 MHz, $D_2O$) δ 8.25 (d, 2H, J=9.0 Hz), 7.28 (d, 2H, J=9.0 Hz), 5.12 (d, 1H, J=3.9 Hz), 4.79 (d, 1H, J=3.7 Hz), 4.51 (d, 1H, J=7.7 Hz), 4.44 (d, 1H, J=7.7 Hz), 4.39 (d, 1H, J=7.7 Hz), 4.31-4.28 (t, 2H, J=7.7 Hz), 4.15-4.11 (m, 2H), 3.99 (d, 1H, J=2.0 Hz), 3.92 (d, 1H, J=2.8 Hz), 3.89-3.44 (m, 33H), 3.16 (t, 1H, J=8.6 Hz), 3.10 (t, 2H, J=6.7 Hz), 2.62 (t, 2H, J=6.9 Hz), 2.20 (t, 2H, J=6.6 Hz), 1.93 (s, 3H), 1.62-1.49 (m, 4H) 1.54-1.48 (m, 2H), 1.45-1.40 (m, 2H), 1.30-1.24 (m, 2H), 1.11 (d, 3H, J=6.5 Hz)

$^{13}$C NMR (150 MHz, D$_2$O) δ178.0, 176.1, 176.0, 156.9, 147.1, 127.3, 124.5, 105.7, 105.0, 103.7, 103.6, 102.2, 101.0, 80.5, 80.0, 78.9, 78.0, 77.8, 77.1, 76.7, 76.4, 76.3, 76.2, 75.2, 74.6, 73.8, 73.5, 72.5, 72.1, 71.8, 71.2, 70.9, 70.8, 70.1, 69.7, 69.5, 68.5, 62.6, 62.6, 62.0, 62.0, 61.7, 53.3, 40.8, 37.1, 35.0, 30.0, 29.7, 26.4, 25.0, 24.1, 23.9, 17.0 HRMS: C$_{55}$H$_{87}$N$_3$O$_{35}$Na [M+Na]$^+$ calculated: 1372.5018; found: 1372.5016.

Example 6

General Procedure for Generating Glycoconjugates

Glycoconjugates were manufactured as follows:

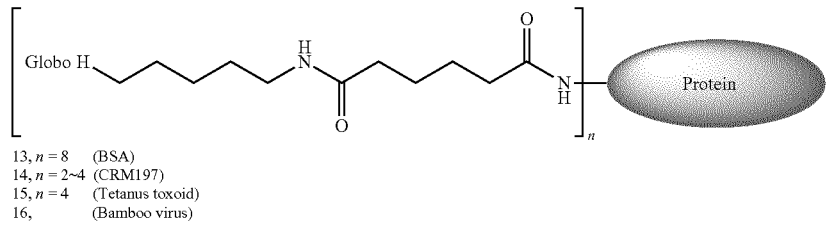

13, n = 8 (BSA)
14, n = 2~4 (CRM197)
15, n = 4 (Tetanus toxoid)
16, (Bamboo virus)

BSA, DT-CRM197, and Tetanus toxoid (Adimmune, Taiwan) was dissolved in 100 mM phosphate buffer pH 7.2 (~5 mg/ml), and 30 to 40 equivalents of Globo H half ester 35 were added to the solution. The mixture was stirred gently for 24 h at room temperature. The mixture was then diluted with deionized water and dialyzed against 5 changes of deionized water. The solution was then lyphophilized to a white powder. The obtained Globo H-protein conjugates can be characterized by MALDI-TOF analysis to determine the carbohydrate incorporation rate. 41 (GH-BSA), MALDI-TOF found 76029, 42 (GH-DT-CRM197) found 62138, 43 (GH-TT) found 162902, 44 (GH-BaMV) was not determined

Example 7

MALDI-TOF MS Analysis for Glycoconjugates

The glycoconjugates 41, 42, 43 and primary carrier proteins were reconstituted with ddH$_2$O (~1 µg/µl). The matrix, sinapinic acid, was freshly prepared with acetonitrile and deionized water 1:1, making final matrix concentration in 10 mg/ml including 0.1% TFA. Gently loaded and mixed the matrix solution and glycoconjugates, then air dried the plate. Calibration was imperative using bovine serum albumin before measurement. Each glycoconjugate and primary protein sample was detected under linear positive mode. The average molecular weight allows the calculation of the average number of carbohydrate incorporated on the carrier protein.

Example 8

Glycan Microarray Fabrication

Microarray were printed (BioDot, Cartesian Technologies, USA) by robotic pin (SMP3, TeleChem International Inc., USA) deposition of ~0.7 nL of various concentrations of amine-containing glycans in printing buffer (300 mM phosphate buffer, pH 8.5 containing 0.005% Tween-20) from a 96 well onto NHS-coated glass slides. Each microarray slide was spotted with 50 µM of nine Globo H analogs (SSEA-4, GH, Gb5, Gb4, Gb3, Gb2, BB4, BB3, and BB2) respectively in 12 replications. Printed slides were allowed to react in an atmosphere of 80% humidity for an hour followed by desiccation overnight. These slides were stored at room temperature in a dessicator before used.

Example 9

Serologic Assay (Glycan Microarray)

Mice sera were diluted 1:60 with 0.05% Tween 20 in 3% BSA/PBS buffer (pH 7.4) as preliminary screening. The glycan microarray was blocked with 50 mM ethanolamine for 1 h, and washed twice with ddH$_2$O and PBS buffer before used.

The serum dilutions were then introduced to the Globo H microarray, and incubated at room temperature for 1 h. The microarray slides were further washed three times with PBST (0.05% Tween-20 in PBS buffer) and PBS buffer, respectively. Next, Cy3-affiniPure goat anti-mouse IgG (H+L), IgG1, IgG2a or anti-mouse IgM was added to the microarray slide and then sealed for 1 hour incubation at room temperature. Finally, the slides were washed three times with PBST, PBS and ddH$_2$O in sequence. The microarray slides were dried before scanned at 532 nm with a microarray fluorescence chip reader (Genepix 4000B). Data were analyzed by software GenePix Pro 6.0 (Axon Instruments, Union City, Calif., USA). To acquire the accurate measurement, PMT gain was adjusted to 400 avoiding fluorescence saturation. The local background was subtracted from the signal at each glycan spot. The spots with obvious defects or no detectable signal were omitted. The ultimate fluorescence intensity was defined as the average of "medians of F532 nm-B532 nm" from replicate spots.

Example 10

Serologic Assay (Enzyme-Linked Immunosorbent Assay)

0.2 µg of Globo-H ceramide in 100 µl carbonate bicarbonate buffer (pH 10) was coated in 96-well plate (NUNC) at 4° C. for overnight. Washed with PBS and blocked with 3% bovine serum albumin for 30 minutes at room temperature. Serial dilutions of mice sera were added into each well and incubated for 1 h at room temperature, followed by washing with DPBST (Dulbecco's Phosphate Buffered Saline, 0.05% Tween20). Goat anti-mouse IgG-AP (1:200, Southern Biotech., USA) was added and incubated for 45 minutes at room temperature. The plates were washed with PBST five times and then incubated with alkaline phosphatase substrate, p-nitrophenyl phosphate (Sigma) for 8 minutes at 37° C. After incubation, the reaction was stopped by adding 3 M NaOH solution and the plates were read at 405 nm on the ELISA reader (SpectraMax, Molecular Devices) The titer was defined as the highest dilution yielding an optical density greater than 0.1.

Example 11

Dosage and Immunization (1) Groups of three mice (6-week-old female C57BL/6 mice, BioLASCO, Taiwan) were administered subcutaneously to abdomen region with GH-KLH (Optimer Inc.), GH-BSA, GH-TT, GH-CRM197, and GH-BaMV respectively with or without glycolipid adjuvant C1 or 7DW8-5 for three times with weekly interval. Each vaccination contained 1 μg of Globo H and with or without 2 μg glycolipid adjuvant. Control mice were injected with phosphate buffer saline (PBS) only. Mice were bled before first immunization (pre-immune) and ten days after third immunization. (2) Groups of three mice (8-week-old female Balb/c mice, BioLASCO, Taiwan) were immunized intramuscularly three times at two weeks interval with GH-BaMV or GH-CRM197 with or without C1, C23, or 7DW8-5, respectively. Each vaccination contained 1.6 μg of Globo H and with or without 2 μg of adjuvant. Control mice were injected with phosphate buffer saline (PBS). Mice were bled before immunization and 2 weeks after each vaccination. (3) Groups of three mice (8-week-old female Balb/c mice, BioLASCO, Taiwan) were immunized with GH-CRM197 or GH-KLH with or without adjuvant C1, C17, 7DW8-5, C30, AlPO$_4$, MF59 (1:1 mixture) as (2) described. All the sera were obtained by centrifugation under 4000 g for 10 minutes. The serologic responses were analyzed by glycan microarray or compared with conventional ELISA assay.

Example 12

Xenograft Model (1) Five groups of immunized female Balb/c mice (PBS, GH-CRM197 alone or with C1, C23 and 7DW8-5, respectively) were injected with 2×10$^5$ metastatic mouse mammary tumor cell lines, 4T1 (in sterile PBS) subcutaneously 8 weeks after final vaccination. (2) Seven groups of immunized female Balb/c mice (GH-KLH alone or with C1, C17, 8-5, C30, AlPO$_4$ and MF59, respectively) were injected with 2×10$^5$ metastatic mouse mammary tumor cell lines, 4T1 (in sterile PBS) subcutaneously 6 weeks after final vaccination. Mice anti-Globo H sera were monitored before and after tumor xenografting. Mice tumor size was measured by Vernier caliper three times per week and defined as (length×height× width)/2 (mm$^3$).

Example 13

Isolation of Primary Tumor Cells from Human Breast Cancer Specimens

Human breast cancer specimens were obtained from patients who had undergone initial surgery at the Tri-Service General Hospital (Taipei, Taiwan). Samples were fully encoded to protect patient confidentiality and were used under a protocol approved by the Institutional Review Board of Human Subjects Research Ethics Committee of Academia Sinica, Taipei, Taiwan. The tumor specimens were sliced to square fragments of 1 mm$^2$ and subjected to enzymatic digestion by incubation in RPMI1640 medium containing collagenase (1,000 U/ml), hyaluronidase (300 U/ml), and DNase I (100 μg/ml) at 37° C. for 2 h. Primary breast tumor cells were collected after filtration through a 100-μm cell strainer (BD Biosciences) and resuspended in RPMI1640 medium supplemented with 5% FBS.

Example 14

Flow Cytometry Analysis

Primary breast cancer cells were prepared as 1×10$^5$ cells in 50 μl of PBS containing 2% FBS and 0.1% NaN$_3$. Cells were labeled with anti-CD24-PE, anti-CD44-APC, and anti-CD45-PerCP-Cy5.5 antibody mixtures (1 μl of each). Globo H expression was detected by staining with monoclonal anti-Globo H antibody (VK-9) conjugated with Alexa488. Analyses were performed on a FACSCanto flow cytometer (Becton Dickinson). BCSCs were defined as CD45$^-$/CD24$^-$/CD44$^+$ cells, and non-BCSCs were defined as other populations of CD45$^-$ cells. Globo H expression was further analyzed in the gated region.

Example 15

Cell Sorting

The cells harvested from human breast tumor engrafted in mice were stained with anti-CD24-PE, anti-CD44-APC, and anti-H2K$^d$-FITC antibody mixtures (BD Biosciences). Fluorescence activated sorting of antibody-labeled cells was carried out on a FACSAria cell sorter (Becton Dickinson). H2 Kd$^-$/CD24$^-$/CD44$^+$ cells were sorted as BCSCs, and other populations of H2 Kd$^-$ cells were sorted as non-BCSCs. The typical purities of BCSCs and non-BCSCs were >85% and >90%, respectively.

Example 16

Immunohistochemistry

For SSEA-4 expression on normal tissues, tissue microarray slides (Biomax) that contained 20 different organs, with each organ derived from five individuals, were used. Slides were dried overnight at 56° C., dewaxed in xylene, and rehydrated according to the standard histopathologic procedures, followed by antigen retrieval with AR-10 solution pH 9.0 (BioGenex Laboratories). SSEA-4 expression was determined with the use of anti-SSEA-4 antibody (eBioscience). Staining for SSEA-4 was detected by using anti-rat IgM as a secondary antibody and was developed by DAB substrate. Slides were counterstained with hematoxylin. Primary breast tumor BC0145 and tumor xenografts from NOD/SCID mice were fixed in 10% phosphate-buffered formalin and embedded in paraffin. Paraffin sections were cut at a thickness of 2 μM, mounted on SuperFrost Plus microscopy slides (Menzel-Gläser), and dried overnight at 55° C. The sections were dewaxed in xylene and rehydrated according to the standard histopathologic procedures, followed by staining with hematoxylin and eosin (H&E). Before immunostaining, the slides were first placed in the solution of 10 mmol/L citrate buffer (pH 6.0) and microwaved for 15 min. The slides were then incubated overnight with anti-ER, or anti-PR antibody. Immunodetection was performed with the Super Sensitive Polymer-HRP IHC Detection System (BioGenex).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

We claim:
1. An immunogenic composition comprising:
(a) a glycan conjugate including a carrier protein, and a glycan comprising Globo H, an immunogenic fragment thereof, or stage-specific embryonic antigen-4 (SSEA-4), wherein the glycan is conjugated with the carrier protein through a linker; and
(b) an adjuvant including C34, which has the structure:

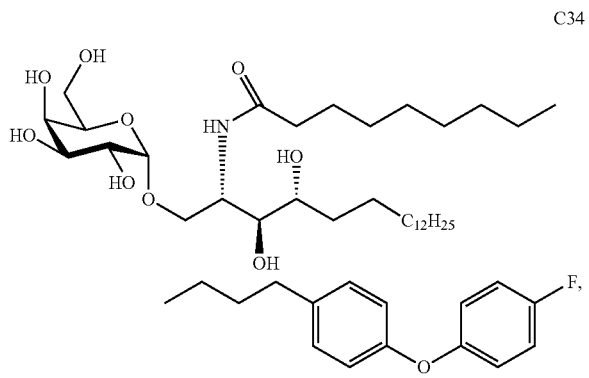

C34 wherein the immunogenic composition induces an immune response that produces a higher relative level of IgG isotype antibodies as compared to IgM isotype antibodies.

2. The immunogenic composition of claim 1, wherein the carrier protein is a toxin protein.

3. The immunogenic composition of claim 2, wherein the toxin protein is diphtheria toxin cross-reacting material 197 (DT-CRM 197), diphtheria toxoid, tetanus toxoid, or bovine serum albumin.

4. The immunogenic composition of claim 1, wherein the linker is a p-nitrophenyl linker.

5. The immunogenic composition of claim 4, wherein the carrier protein is DT-CRM 197.

6. The immunogenic composition of claim 1, wherein the carrier protein is DT-CRM 197.

7. The immunogenic composition of claim 1, wherein the antibodies generated by the immune response specifically binds to at least one of the antigens selected from the group consisting of Globo H, Gb4, stage-specific embryonic antigen-3 (SSEA-3) and SSEA-4.

8. A cancer vaccine comprising:
(a) an immunogenic composition containing (i) a glycan conjugate containing a carrier protein, and a glycan comprising Globo H, wherein the glycan is conjugated with the carrier protein through a linker, and (ii) an adjuvant including C34; and
(b) a pharmaceutically acceptable excipient;
wherein the immunogenic composition induces an immune response that produces a higher relative level of IgG isotype antibodies as compared to IgM isotype antibodies.

9. The cancer vaccine of claim 8, wherein the carrier protein is DT-CRM 197.

10. The cancer vaccine of claim 9, wherein the cancer is an epithelial-derived cancer.

11. A therapeutic against breast cancer stem cells, the therapeutic comprising (i) Globo H conjugated through a linker with DT-CRM 197; and (ii) an adjuvant including C34.

12. The therapeutic of claim 11, wherein administration of the therapeutic to a subject induces production of antibodies that recognize Globo H expressed on a breast cancer stem cell.

13. The immunogenic composition of claim 1, wherein the glycan is Globo H or SSEA-4 or is the immunogenic fragment Bb4, Gb4, or SSEA-3.

14. The immunogenic composition of claim 13, wherein the glycan is Globo H.

15. The immunogenic composition of claim 13, wherein the glycan is the immunogenic fragment SSEA 3.

16. The immunogenic composition of claim 13, wherein the glycan is SSEA 4.

17. The immunogenic composition of claim 14, wherein the carrier protein is DT-CRM 197.

18. The immunogenic composition of claim 15, wherein the carrier protein is DT-CRM 197.

19. The immunogenic composition of claim 16, wherein the carrier protein is DT-CRM 197.

* * * * *